United States Patent
Taube

(10) Patent No.: US 11,092,984 B1
(45) Date of Patent: Aug. 17, 2021

(54) OXYGEN MIXING AND DELIVERY

(71) Applicant: Vapotherm, Inc., Exeter, NH (US)

(72) Inventor: John C. Taube, Raleigh, NC (US)

(73) Assignee: Vapotherm, Inc., Exeter, NH (US)

( * ) Notice: Subject to any disclaimer, the term of this patent is extended or adjusted under 35 U.S.C. 154(b) by 0 days.

(21) Appl. No.: 16/722,722

(22) Filed: Dec. 20, 2019

Related U.S. Application Data

(63) Continuation of application No. 16/003,508, filed on Jun. 8, 2018, now Pat. No. 10,514,662, which is a
(Continued)

(51) Int. Cl.
  *G05D 11/13* (2006.01)
  *G05B 13/02* (2006.01)
  (Continued)

(52) U.S. Cl.
  CPC .......... *G05D 11/13* (2013.01); *A61M 16/024* (2017.08); *G05B 13/0205* (2013.01); *A61M 16/125* (2014.02); *A61M 16/16* (2013.01); *A61M 16/161* (2014.02); *A61M 2202/0208* (2013.01); *A61M 2205/13* (2013.01); *A61M 2205/18* (2013.01);
  (Continued)

(58) Field of Classification Search
  CPC .... A61M 2202/0208; A61M 2230/205; A61M 2205/3368; A61M 2205/18; A61M 16/024; A61M 16/161; A61M 2230/06; A61M 16/06; A61M 2205/0208; A61M 2205/8262; A61M 2230/206;
  (Continued)

(56) References Cited

U.S. PATENT DOCUMENTS

| | | |
|---|---|---|
| 2,414,747 A | 1/1947 | Kirschbaum |
| 3,734,091 A | 5/1973 | Taplin |
| (Continued) | | |

FOREIGN PATENT DOCUMENTS

| | | |
|---|---|---|
| CA | 2545570 A1 | 9/2005 |
| CA | 2691377 A1 | 1/2009 |
| (Continued) | | |

OTHER PUBLICATIONS

Branson, et al., "Is Humidification Always Necessary During Non-invasive Ventilation in the Hospital?", Respiratory Care, vol. 55, No. 2, Feb. 2010.
(Continued)

*Primary Examiner* — Tuan C Dao
(74) *Attorney, Agent, or Firm* — NK Patent Law

(57) ABSTRACT

An adaptive gas mixture controller system. A pulse oximeter interface receives pulse oximeter data. A gas blender interface communicates with a separate externally connected gas blender. A processor receives pulse oximeter data via the pulse oximeter interface and outputs data to the gas blender interface for adaptive feedback control of the gas mixture based upon the $SpO_2$ level signals from the pulse oximeter interface. When the processor receives data from the gas blender indicating that the gas mixture has been manually changed, enters a manual override mode and halts sending adaptive feedback control signals to the gas blender. This abstract is not to be considered limiting, since other embodiments may deviate from the features described in this abstract.

44 Claims, 11 Drawing Sheets

Related U.S. Application Data continuation of application No. 14/602,392, filed on Jan. 22, 2015, now Pat. No. 10,007,238.

(51) Int. Cl.
*A61M 16/00* (2006.01)
*A61M 16/16* (2006.01)
*A61M 16/12* (2006.01)

(52) U.S. Cl.
CPC .......... *A61M 2205/3368* (2013.01); *A61M 2205/502* (2013.01); *A61M 2205/8206* (2013.01); *A61M 2205/8262* (2013.01); *A61M 2230/06* (2013.01); *A61M 2230/205* (2013.01)

(58) Field of Classification Search
CPC .......... A61M 16/16; A61M 16/125; A61M 2202/02; A61M 2205/7545; G05B 13/0205; G05D 11/13
See application file for complete search history.

(56) References Cited

U.S. PATENT DOCUMENTS

| | | | |
|---|---|---|---|
| 4,325,413 A | 4/1982 | Lenhart et al. | |
| 4,584,996 A | 4/1986 | Blum | |
| 4,665,911 A | 5/1987 | Williams et al. | |
| 4,765,340 A | 8/1988 | Sakai et al. | |
| 4,889,116 A | 12/1989 | Taube | |
| 5,003,985 A | 4/1991 | White et al. | |
| 5,103,814 A | 4/1992 | Maher | |
| 5,178,151 A | 1/1993 | Sackner | |
| 5,388,575 A | 2/1995 | Taube | |
| 6,186,142 B1 | 2/2001 | Schmidt et al. | |
| 6,561,187 B2 | 5/2003 | Schmidt et al. | |
| 7,329,038 B2 | 2/2008 | Hashiba | |
| 7,591,632 B2 | 9/2009 | Baecke et al. | |
| 7,802,571 B2 | 9/2010 | Tehrani | |
| 8,194,944 B2 | 6/2012 | Tivig et al. | |
| 8,434,481 B2 | 5/2013 | Ogilvie et al. | |
| 8,434,483 B2 | 5/2013 | Patel et al. | |
| 8,434,484 B2 | 5/2013 | Patel | |
| 8,434,523 B2 | 5/2013 | Suharno | |
| 8,670,811 B2 | 3/2014 | OReilly | |
| 8,720,439 B1 | 5/2014 | Kolkowski et al. | |
| 8,801,619 B2 | 8/2014 | Baker, Jr. et al. | |
| 9,272,623 B2 | 3/2016 | Masuda | |
| 9,724,025 B1 | 8/2017 | Kiani et al. | |
| 9,775,570 B2 | 10/2017 | Al-Ali | |
| 9,788,735 B2 | 10/2017 | Al-Ali | |
| 10,007,238 B1 | 6/2018 | Taube | |
| RE47,218 E | 2/2019 | Al-Ali | |
| 10,532,169 B2 | 1/2020 | Eberhard et al. | |
| RE47,882 E | 3/2020 | Al-Ali | |
| 10,674,948 B2 | 6/2020 | Diab et al. | |
| 2001/0035185 A1* | 11/2001 | Christopher | A61M 16/0683 128/204.17 |
| 2002/0017302 A1 | 2/2002 | Fukunaga et al. | |
| 2003/0013980 A1 | 1/2003 | Starr et al. | |
| 2003/0211244 A1 | 11/2003 | Li et al. | |
| 2003/0216285 A1* | 11/2003 | Dumont | A61K 35/19 514/1 |
| 2004/0054261 A1 | 3/2004 | Kamataki et al. | |
| 2004/0230108 A1* | 11/2004 | Melker | A61B 5/0261 600/340 |
| 2005/0051168 A1* | 3/2005 | DeVries | A61M 16/0063 128/204.21 |
| 2005/0109340 A1 | 5/2005 | Tehrani | |
| 2005/0222503 A1* | 10/2005 | Dunlop | A61B 5/4094 600/323 |
| 2005/0247311 A1* | 11/2005 | Vacchiano | A61M 16/0045 128/203.12 |
| 2007/0137107 A1* | 6/2007 | Barnicki | C10K 1/007 48/198.3 |
| 2008/0156328 A1 | 7/2008 | Taube | |
| 2008/0183057 A1 | 7/2008 | Taube | |
| 2009/0090363 A1 | 4/2009 | Niland et al. | |
| 2009/0305214 A1* | 12/2009 | Pybus | A61M 5/486 434/268 |
| 2010/0175695 A1* | 7/2010 | Jamison | A61M 16/12 128/203.14 |
| 2010/0224191 A1* | 9/2010 | Dixon | A61B 5/14539 128/204.23 |
| 2011/0067697 A1* | 3/2011 | Lellouche | A61M 16/026 128/204.23 |
| 2011/0152648 A1 | 6/2011 | Rustick | |
| 2011/0190611 A1 | 8/2011 | Rabi | |
| 2011/0200392 A1 | 8/2011 | Moncrief, III | |
| 2011/0319783 A1 | 12/2011 | Lindholt et al. | |
| 2012/0016219 A1 | 1/2012 | Fujii | |
| 2012/0090611 A1 | 4/2012 | Graboi et al. | |
| 2012/0325207 A1 | 12/2012 | Fromage | |
| 2013/0030267 A1 | 1/2013 | Lisogurski et al. | |
| 2013/0174841 A1* | 7/2013 | McAuley | A61M 16/0666 128/203.14 |
| 2013/0276780 A1 | 10/2013 | Tobia et al. | |
| 2014/0166005 A1 | 6/2014 | Tatkov et al. | |
| 2015/0032029 A1 | 1/2015 | Al-Ali et al. | |
| 2015/0059754 A1 | 3/2015 | Chbat et al. | |
| 2015/0107588 A1* | 4/2015 | Cheung | A61M 16/0003 128/203.14 |
| 2015/0112169 A1 | 4/2015 | Lamego et al. | |
| 2015/0320953 A1 | 11/2015 | Acker et al. | |
| 2016/0029932 A1 | 2/2016 | Al-Ali | |
| 2016/0121063 A1 | 5/2016 | Tatkov et al. | |
| 2016/0361508 A1* | 12/2016 | Cohen | A61M 16/109 |
| 2017/0042488 A1 | 2/2017 | Muhsin | |
| 2017/0143538 A1 | 5/2017 | Lee et al. | |
| 2017/0312471 A1 | 11/2017 | Anger et al. | |
| 2018/0146902 A1 | 5/2018 | Kiani et al. | |
| 2018/0310822 A1 | 11/2018 | Indorf et al. | |
| 2019/0029578 A1 | 1/2019 | Al-Ali et al. | |
| 2019/0192076 A1 | 6/2019 | McHale et al. | |
| 2019/0200941 A1 | 7/2019 | Chandran et al. | |

FOREIGN PATENT DOCUMENTS

| | | |
|---|---|---|
| CA | 2827253 A1 | 9/2012 |
| WO | 9624402 | 8/1996 |
| WO | WO2002056931 A2 | 7/2002 |
| WO | WO2005038690 A2 | 4/2005 |
| WO | WO2005051280 A2 | 6/2005 |

OTHER PUBLICATIONS

Anon., "Critical Care Therapy and Respiratory Care Section", National Institutes of Health, 1112000.

Sano, et al., Adaptive control of arterial oxygen pressure of newborn infants under incubator oxygen treatments, IEE Proceeding, vol. 132, Pt. D., No. 5, Sep. 1985.

Anon., "Analog Dialogue: Pulse Oximeter", Analog Devices, Inc., 1995-2014.

Soto, et al., "Automatic Ventilation Control", Freescale.com/beyondbits, undated, downloaded Sep. 17, 2014.

Elleau, et al., "Helium-Oxygen mixture in respiratory distress syndrome: a double blind study", J Pediatr., 122(1):132-6, Abstract, Jan. 1993.

Davies, et al., "Inspired Gas Temperature in Ventilated Neonates", Pediatric Pulmonology 38:50-54, 2004.

Carter, et al., "Evaluation of heliox in children hospitalized with acute sever asthma. A randomized crossover trial", Abstract, Chest, 109(5):1256-61, May 1996.

Adawy, et al., "Design of Fuzzy Controller for Supplying Oxygen in Sub-acute Respiratory Illnesses", IJCSI, vol. 9, Issue 3, No. 1, May 2012.

Kass, et al., "Heliox therapy in acute severe asthma", Abstract, Chest, 107(3):757-60, Mar. 1995.

Kudukis, et al., "Inhaled helium-oxygen revisited: effect of inhaled helium-oxygen during the treatment of status asthmaticus in children", Abstract, J Pediatr., 130(2):217-24, Feb. 1997.

(56) References Cited

OTHER PUBLICATIONS

Lu, et al., "Helium-Oxygen in Treatment of Upper Airway Obstruction", Anestheology, vol. 45, Dec. 1976.
Manthous, et al., "Heliox improves pulsus paradoxus and peak expiratory flow in nonintubated patients with severe asthma", Am J Respir Crit Care Med. Abstract, 151(2pt 1):310-4, Feb. 1995.
Martin-Barbaz, et al., "Use of helium oxygen mixtures in status asthmaticus", Abstract, Rev Pneumol Clin. 43(4):186-9, 1987.
Anon.,"MR850 Respiratory Humidifier", Fisher & Paykel, REF 185042343, Rev. J, Aug. 2012.
Anon., "Oxygen Saturation", date unknown, downloaded Aug. 20, 2014.
Alkurawy, "Design of an Efficient Controller for Arterial Oxygen Saturation in Neonatal Infants", PhD Thesis, University of Missouri-Columbia, Dec. 2013.
Sauder, et al., "Helium-oxygen and conventional mechanical ventilation in the treatment of large airway obstruction and respiratory failure in an infant", Abstract, South Med J. 84(5):646-8, May 1991.
Shiue, et al., "The use of helium-oxygen mixtures in the support of patients with status asthmaticus and respiratory acidosis", J Asthma, Abstract, 26(3)177-80, 1989.
Swidwa, et al., "Helium-oxygen breathing in severe chronic obstructive pulmonary disease", Abstract, Chest, 9=87(6):790-5, Jun. 1985.
Panchal, et al., "Feedback-Controlled System to Titrate Oxygen Delivery", Drexel University, Winter 2014.
Ardizzoni, "The incredible versatile op amp in medical apps", Analog devices, Nov. 2, 2009.
Wolfson, et al., "Mechanics and energetics of breathing helium in infants with bronchopulmonary dysplasia", Abstract, J Pediatr, 104(5):752-7, May 1984.
USPTO, Non-Final Rejection in U.S. Appl. No. 16/003,508 dated Jun. 27, 2019.
USPTO, Non-Final Rejection in U.S. Appl. No. 14/602,392 dated Oct. 3, 2017.
USPTO, Final Office Action in U.S. Appl. No. 14/602,392 dated Mar. 1, 2018.
PCT, International Search Report and Written Opinion in International application No. PCT/US2020/057823 dated Jan. 28, 2021.
PCT, International Search Report and Written Opinion in International application No. PCT/US2020/062118 dated Mar. 11, 2021.

\* cited by examiner

OXYGEN MIXING AND DELIVERY

CROSS-REFERENCE TO RELATED APPLICATIONS

This application is a continuation application of U.S. patent application Ser. No. 16/003,508, filed on Jun. 8, 2018, which is a continuation application of U.S. patent application Ser. No. 14/602,392, filed on Jan. 22, 2015, the entire contents of which are hereby incorporated herein by reference.

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND

Oxygen mixing and delivery systems are used to blend concentrated oxygen with ambient air and/or other gasses in order to provide for delivery (infusion) of the blended gasses to a patient to assist in breathing. Such systems may utilize invasive (active) delivery to the patient for example by use of endotracheal tubes, or may provide delivery of the gasses in a non-invasive (passive) manner such as by use of a cannula or mask.

BRIEF DESCRIPTION OF THE DRAWINGS

Certain example embodiments illustrating organization and method of operation, together with objects and advantages may be best understood by reference detailed description that follows taken in conjunction with the accompanying drawings in which.

GLOSSARY

Figure 1:
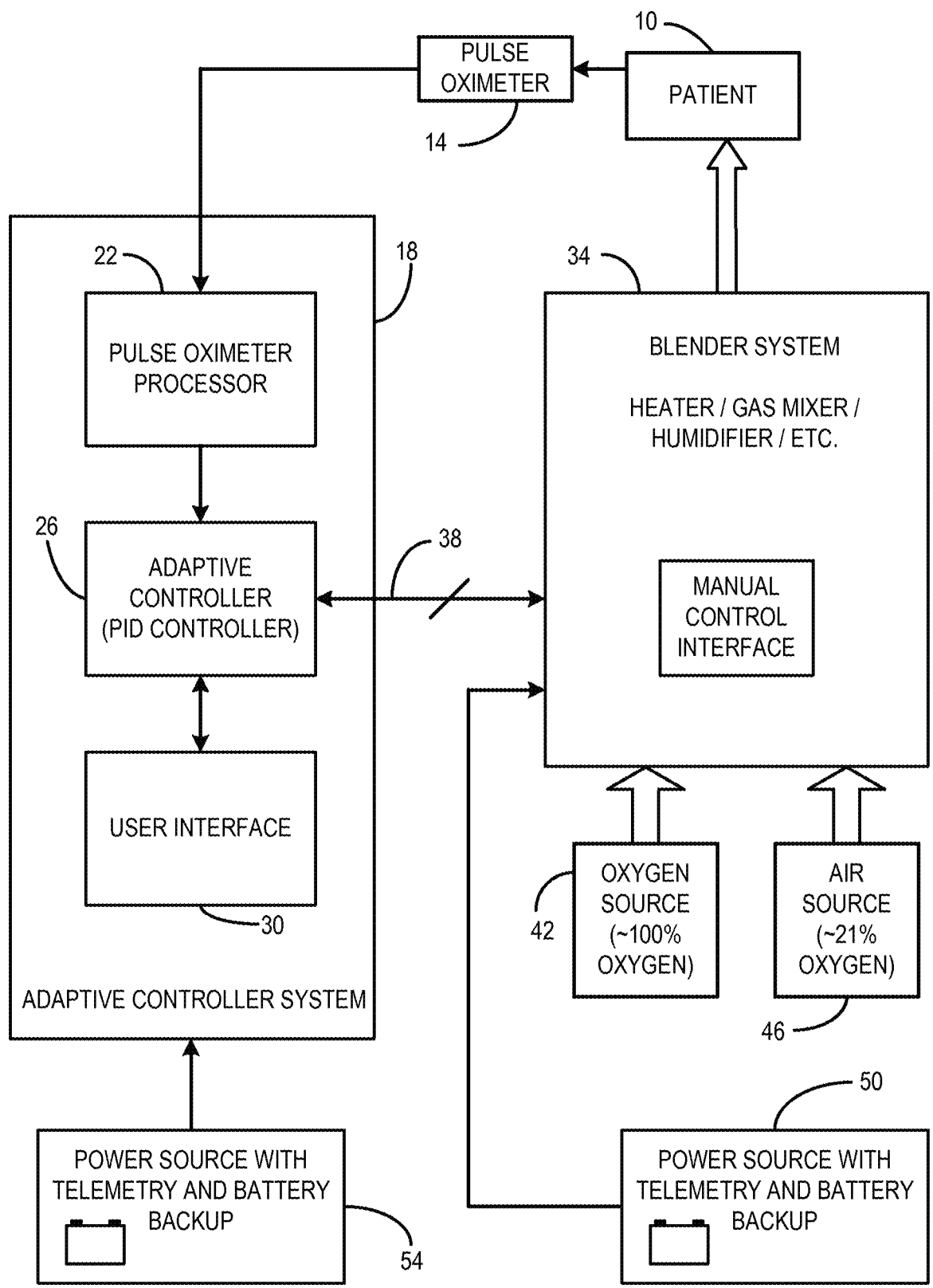
FIG. 1 is a block diagram of an example of an oxygen mixing and delivery system which is consistent with certain example embodiments of the present invention.

Reference throughout this document to "one embodiment", "certain example embodiments", "examples", "an embodiment", "an example", "an implementation" or similar terms means that a particular feature, structure, or characteristic described in connection with the embodiment, example or implementation is included in at least one embodiment, example or implementation of the present invention. Thus, the appearances of such phrases or in various places throughout this specification are not necessarily all referring to the same embodiment, example or implementation. Furthermore, the particular features, structures, or characteristics may be combined in any suitable manner in one or more embodiments, examples or implementations without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

The term "coupled", as used herein, is defined as connected, although not necessarily directly, and not necessarily mechanically.

The term "program" or "computer program" or similar terms, as used herein, is defined as a sequence of instructions designed for execution on a computer system. A "program", or "computer program", may include a subroutine, a function, a procedure, an object method, an object implementation, in an executable application, an app, a widget, an applet, a servlet, a source code, an object code, a sketch, a shared library/dynamic load library and/or other sequence of instructions designed for execution on a computer system.

The term "processor", "controller", "CPU", "Computer" and the like as used herein encompasses both hard programmed, special purpose, general purpose and programmable devices and may encompass a plurality of such devices or a single device in either a distributed or centralized configuration without limitation.

The term "SpO$_2$" is an acronym for "Saturation of Peripheral Oxygen". Within the related technology, the term SpO$_2$ is often casually referred to as "blood oxygen", "blood oxygen saturation", "blood oxygen concentration" and other similar terms. While any suitable measurement of "oxygen saturation" can be used in a manner consistent with Applicant's teachings herein, one implementation uses SpO$_2$. SpO$_2$ is used as an estimation of blood oxygen concentration and is usually measured with a pulse oximeter.

The term "solenoid valve" or simply "solenoid" means a valve device that is used to control two or more gasses from two or more inputs to direct the gasses to a single output.

The term "bi-modal solenoid valve" or simply "bi-modal solenoid" means a type of solenoid valve device which allows only one gas from one of its inputs to be directed to a single output based upon control signals. For example, the proportion of mixture of two gasses can be controlled by controlling the amount of time each input is directed to the output.

The term "proportional solenoid valve" or simply "proportional solenoid" is used to refer to a type of solenoid valve device in which two or more gasses from two or more inputs can be controlled in a manner that allows each input to be directed to the output proportionally so that, for example, one input may be set to 30% of full flow while the other input may be set to 70% full flow. This proportionality can be controlled either by signals that cause the valves to open and close in proportion to one another, or by signals that individually select the degree to which each valve is open or closed.

The term "invasive" is used to describe the active delivery of gasses to a patient by use of an endotracheal tube or the like.

The term "non-invasive" is used to describe more passive delivery of gasses to a patient by use of a mask or cannula or the like.

A "pulse oximeter" is a photoelectric device that measures the amount of saturated hemoglobin in the tissue capillaries by transmitting beams of light through the tissue to a light receiver. A pulse oximeter is generally configured so as to clip onto a fingertip or earlobe. The amount of saturated hemoglobin affects the wavelength and reflection or transmission of the light transmitted through the tissue. By analyzing the received light, a percentage of oxygen saturation ($SpO_2$) of the blood can be deduced. Commercially available pulse oximeters often also provide for measurement of a pulse as well as generating various alarm condition signals.

The term "smart" is intended to designate an operational mode in which the oxygen delivery rate is adaptively feedback controlled as opposed to manual control.

The term "$PaO_2$" means the partial pressure of atrial oxygen.

The term "$FiO_2$" means fraction of inspired oxygen and in this discussion represents a blend of gas delivered to the patient.

The term "button" is used to mean a switch that makes a user selection in a user interface and may be realized as an electromechanical switch or as a virtual button displayed on, e.g., a touchscreen display.

A proportional-integral-derivative controller (PID controller) is a control loop feedback controller. A PID controller calculates an error value as the difference between a measured process variable and a desired value of the process variable (or set point). The controller operates to minimize the difference between the measured value and the set point. A PID controller accomplishes this by use of an algorithm that uses three separate parameters—proportional (P), integral (I) and derivative (D) values interpreted at discrete increments of time where P depends on the current error, I depends of the accumulation of past errors, and D predicts future errors. The weighted sum of these three actions is used to adjust a process—in this case the proportion of oxygen represented by $FiO_2$. Mathematically, these values are generally represented by the following equations.

$$P = K_p \varepsilon(t) \quad \text{(Eqn. 1)}$$

$$I = K_i \int_0^t e(\tau) d\tau \quad \text{(Eqn. 2)}$$

$$D = K_d \frac{de(t)}{dt} \quad \text{(Eqn. 3)}$$

where the oxygen mixer control signal is derived from the PID controller output $u_t$:

$$u_t = P + I + D = K_p e(t) + K_i \int_0^t e(t) dt + K_d \frac{de(t)}{dt} \quad \text{(Eqn. 4)}$$

and where:
$K_p$: Proportional gain coefficient;
$K_i$: Integral gain coefficient;
$K_d$: Derivative gain coefficient;
e: Error, difference between measured and target;
t: Time; and
τ: Integration variable; takes on values from time 0 to present time t.

For purposes of this document, a controller may be referenced as a PID controller for convenience and by way of example, but in practice the controller may in fact not use all three of the elements of Proportional, Integral and Derivative control. Use of only one or two of the PID control functions is common and use of other feedback control mechanisms is also within the scope of the present teachings.

DETAILED DESCRIPTION

While this invention is susceptible of embodiment in many different forms, there is shown in the drawings and will be herein described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

In accord with certain example embodiments consistent with the present invention, a gas blending system is provided in which a gas is delivered to a patient. The gas is usually a mixture of oxygen and air (and/or other gasses) to achieve a desired percentage of oxygen in the mixture. In certain embodiments, the gas blending system also provides for heating and humidification of the gas mixture and measurements of the heat and humidity of the supplied gas mixture. A feedback mechanism is provided in which the gas blending system provides data to separate adaptive controller system including data relating to the gas mix, gas temperature, flow rate, humidity etc. Data from a pulse oximeter attached to the patient provides data to the adaptive controller system so that the adaptive control system can control the percentage of oxygen delivered to the patient via the blender system in order to achieve a target $SpO_2$. Many variations will occur to those skilled in the art upon consideration of the present teachings.

Turning now to FIG. 1, an illustrative example of an oxygen mixing and delivery system is depicted in which a patient 10 is to be provided with a gas mixture to treat any number of breathing disorders, or to provide for respiration during surgical procedures, etc. The patient 10 is fitted with a pulse oximeter 14 that measures the blood oxygen level in the form of a $SpO_2$ measurement (which is the output that is conventionally provided by a pulse oximeter).

The pulse oximeter acquires the percentage of a patient's arterial blood oxygen $SpO_2$ as well as the patient's pulse rate. The $SpO_2$ and pulse rate acquired from the patient is input to an adaptive controller system 18 that is based upon one or more programmed or hardwired processor/controllers for use as a feedback signal for calculating a percentage of oxygen to be delivered to the patient. The adaptive controller system 18 can be used with ventilators, continuous flow systems, oxygen diluters and benders, collectively and individually referred to herein as blender systems.

Commercially available pulse oximeters such as 10 include mechanisms for detecting not only pulse rate and SpO$_2$ levels, but most also detect at least the conditions of: the sensor on or off the patient, the sensor being disconnected and low perfusion. Other sensors can detect other parameters that can be conveyed to the adaptive controller system 18 and can be used to provide enhanced alarm detection and other operational parameters.

As illustrated, the pulse oximeter 14 delivers data measured on the patient 10 to a pulse oximeter processor 22 forming part of the adaptive controller system 18. The adaptive controller system may be configured to accept connection to any number of different commercially available pulse oximeters, thereby increasing the flexibility of the system. Pulse oximeter processor 22 in turn converts the data into a form best processed by an adaptive controller 26 and delivers the data to 26. Adaptive controller 26 is programmed to operate as deemed appropriate by medical personnel via a user interface 30 forming a part of the system 18 to provide a prescribed amount of a gas mixture to a patient in order to provide therapy. The feedback data from the pulse oximeter 14 is used by the adaptive controller to control the oxygen concentration delivered to the patient to achieve a target SpO$_2$ peripheral blood oxygen level. In the implementation depicted, this control is via a PID controller forming a part of the adaptive controller 26.

Adaptive controller 26 communicates with a blender system 34 via a wired or wireless communication bus 38 using any suitable communication protocol. In certain implementations, the protocol can be, for example, a serial bus interface, a parallel bus interface, an Ethernet interface, IEEE 1394 interface, a Universal Serial Interface (USB) or any other suitable interface including proprietary interfaces. Further, data relating to the patient's condition and the gas being provided to the patient can be provided to remote systems for display to personnel who monitor multiple patients, for example, using additional communication interfaces (not shown).

In accord with the present teachings, the blender system 34 is a separate device that is packaged in a separate housing and which can be produced by any number of different manufacturers and adapted to receive adaptive control from the system 18. Generally, the blender system 34 can operate as a standalone gas delivery system that is operable under manual control by medical personnel. By use of separate blender system and adaptive controller system, multiple blender systems may be deployed and adapted to various specialized usage at reduced cost and complexity when adaptive control is not deemed desirable. Thus, in instances where adaptive control is not deemed suitable by medical personnel, the blender system can be utilized as a standalone manually controlled device. This decreases overall cost and a reduced number of adaptive controller systems 18 can be utilized where deemed appropriate without increasing the cost of each blender system deployed in a medical treatment facility.

In certain example embodiments, the blender system 34 receives compressed gasses from an oxygen source 42 that provides approximately 100% oxygen and from a source 46 of compressed air containing oxygen at approximately 21% oxygen. These gasses, and possibly others, can be combined using known techniques such as, for example, the oxygen blending system disclosed in U.S. Pat. No. 5,388,575, which is hereby incorporated by reference, and others.

In the present example system, the blender system 34 and the adaptive controller system 18 are provided as separate units that are contained in separate mechanical housings that are interconnected by a bus connection 38. This enables the blender system 34 to conveniently operate under manual override control in order to override a malfunctioning adaptive controller system 18, or alternatively, to override the adaptive controller system so as to permit the care provider to implement emergency measures in critical medical situation. Power is supplied to the blender system using an AC power source 50 coupled to a facility's power infrastructure (e.g., the 120 volt line available in the U.S.) as well as a battery backup to assure continuous delivery of the gasses to the patient in the event of a power failure (such systems are often referred to as a UPS or Uninterruptable Power Source). Similarly, a separate AC power source 54 is coupled to the adaptive controller system 18. By providing these functions as separate devices, an interface can be provided that allows use of the adaptive controller system 18 with a variety of blender and gas delivery systems, potentially from multiple manufacturers. Further, such blender systems and gas delivery systems can include those that are capable of manual control that can operate standalone for more stable patients that are not in need of an adaptive controller system to regulate their SpO$_2$ level. Power sources 50 and 54 may be integral to systems 34 and 18 respectively.

It is noted that in the system as depicted, certain analog signals are shown to be received by the various processors. It is to be understood that analog to digital conversion or digital to analog conversion is carried out as called for to render the various signals compatible. The details of such conversions are omitted from these illustrations for clarity.

In accord with one example implementation, the system described by way of example herein can provide control of the gases to provide a gas flow rate (between about 1 and 60 litres/minute (LPM)); a high temperature alarm limit with a tracking alarm limit of about ±2.0° C.; a humidity output of greater than about 33 mg H$_2$O/L at about 37° C. when used in an invasive mode (e.g., by use of an endotracheal tube or the like); a humidity output of greater than about 10 mg H$_2$O/L at 37° C. when used in non-invasive mode (e.g., by use of a mask or cannula); and an alarm limit of SpO$_2$ below about 90%. Some or all of these values may be assigned by medical personnel.

Figure 2:
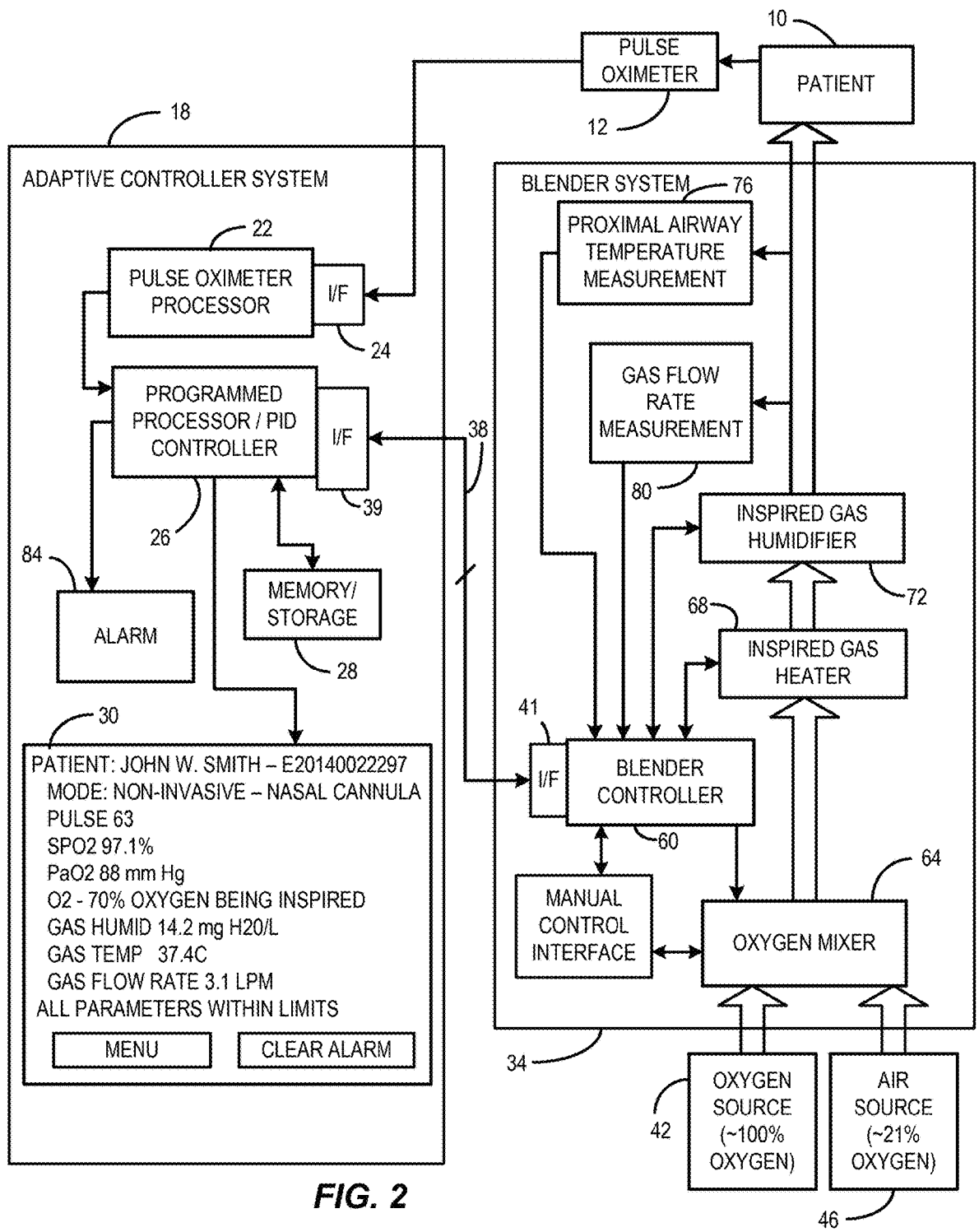
FIG. 2 is a more detailed block diagram of an example of an oxygen mixing and delivery system which is consistent with certain example embodiments of the present invention.

Referring now to FIG. 2, in accord with certain example implementations consistent with the present teachings, a more detailed depiction of an example system consistent with the present teachings is shown. The adaptive controller system 18 includes adaptive controller 26 that incorporates a programmed processor or hard wired processor circuit configured to run a proportional-integral-differential (PID) control process (or other suitable feedback control process) that uses the SpO$_2$ as measured by the pulse oximeter 12 and received by the pulse oximeter processor 22 via a suitable interface 24 as an input for calculation of an oxygen concentration percentage (FiO$_2$) that is to be delivered to the patient. Interface 24 can be any suitable interface including those that have been standardized by various manufacturers of pulse oximeters and may incorporate multiple interfaces for connection to pulse oximeters made by multiple manufacturers. Processor 26 utilizes non-transitory storage and memory 28 for storage of data and programming instructions.

The output of the adaptive controller system 18 provides signals to the blender system's controller 60 and receives further feedback information from controller 60 via bus 38. In one example embodiment, the bus 38 is a conventional serial bus that is coupled between processor 26 and controller 60 via interface circuits 39 and 41 respectively. In certain implementations, a standard EIA/TIA-232-E serial interface operating at 38400 baud, with no parity bits, 8 data bits and 2 stop bits can be used. Other suitable interfaces can also be utilized without limitation.

Blender Controller 60 controls an oxygen mixer device 65 which uses sources of approximately 100% oxygen 42 and air (having approximately 21% oxygen) 46 to form a blended gas having a desired $FiO_2$ as calculated for administration as an inspired gas to the patient 10. A control algorithm that represents the respiratory physiology of the patient is used by the PID controller embodied in processor 26. The oxygen mixer device 64 may, for example, utilize a proportional solenoid valve system or may use a bi-modal solenoid valve system or any other suitable gas mixing arrangement.

The PID controller of 26 calculates the desired $FiO_2$ to be generated by the oxygen mixer 64 and controls the oxygen mixer 64 in order to achieve the calculated gas mixture to obtain or maintain a target $SpO_2$.

User interface 30 can be any suitable mechanism for input/output of user commands and display of relevant data. In certain example embodiments, the interface 30, under control of processor 26 supports a display range of $O_2$ supplied by the mixer 64 of about 21% to 100%. Further, the interface 30, under control of the processor 26 supports a display range for informing the user of the patient's $SpO_2$ between at least about 70 to 100%, and a pulse rate display of at least about 50 to 200 beats per minute (BPM). In certain embodiments, no state change or behavior change occurs when buttons are pressed or other user actions are input if those actions or buttons are designated as currently inactive.

In the example shown, oxygen mixer 64 receives gases of approximately 100% oxygen from oxygen source 42 and air having approximately 21% oxygen from source 46 (which may be ambient air or pressurized ambient air) to form a blended gas output. The gas blending may be accomplished in several ways. In one example, a bi-modal solenoid valve is used to alternately pass each input gas from sources 42 and 46 to the output of the solenoid valve (not shown). The output may be blended in a chamber prior to delivery to the output of the oxygen mixer. In this example implementation, the percentage of oxygen is adjusted by the relative amount of time each of the inputs to the solenoid valve is coupled to the solenoid output. Thus, the processor 60 (either under control of processor 26 or under manual override control) controls the percentage of oxygen at the output of the mixer 64 by toggling between each input port to produce a blended gas at the output port of the bi-modal solenoid valve. This output can be further mixed in a chamber as previously noted.

In another example embodiment, a proportional solenoid valve can be used to achieve the blending of the gases. In this embodiment, the proportional solenoid receives oxygen from source 42 and air from source 46. The processor 60 similarly controls the proportional solenoid so as to adjust the mixture of gas. This is done in this example by controlling a percentage of gas passed from each input of the proportional solenoid valve to the output to produce the blended gas of desired percentage oxygen. A mixing chamber may be used or omitted from this implementation since the gasses will generally adequately blend in the proportional solenoid valve and lines to the patient 10.

When supplemental gases are administered to a patient, the gases can be uncomfortably cool—in part due to the expansion of the gases from their pressurized sources when released to the oxygen mixer 64. Further, the mixed gases may be uncomfortably dry causing a drying of the patient's nasal tissues. In order to enhance the comfort to the patient, in certain example implementations the blender system 34 may incorporate a heater 68 that heats the gas mixture from oxygen mixer 64. Similarly, the gas mixture can be humidified by a humidification device 72 (either or both).

In this case, as the blended gas is output by the oxygen mixer 64, the blended gas travels through a heating and humidification system made up of heater 68 and humidifier 72. The heating and humidification system heats and humidifies the respiratory gases delivered via endotracheal tubes, nasal cannula or face mask to adult, pediatric, infant and neonatal patients. The heating device 68 can utilize any heating mechanism including electrically resistive heating, heated wire heating, Peltier effect heating, etc.

The humidifier 72 can be realized using any suitable humidification arrangement. In one example embodiment, the humidifier 38 uses a humidifier cartridge fed by a sterile water reservoir using any suitable vaporization mechanism including ultrasonic vibration or heating to steam. In other example embodiments, the gasses air can be bubbled through a sterile water reservoir to increase the humidity of the gas mixture. Other variations will occur to those skilled in the art upon consideration of the present teachings.

Humidifier 72 can provide data to the processor 60 indicating the rate at which water is being consumed or other measure of humidity. This can be correlated with the amount of gas being delivered to determine the level of humidification of the gases. In certain example implementations, the processor 60 can control the humidification level of humidifier 72 using any suitable control mechanism (e.g., blending with un-humidified gas mixture, reduction of level of vaporization, etc.) in order to maintain a target water vapor content in the gases.

The temperature of the gases can be measured using a thermistor or other heat sensing element that is operatively approximately proximal to the point of delivery to the patient via temperature measurement device 76 that can reside inside the gas delivery tubes at a location close to the patient to produce temperature data (i.e., a device that measures resistance of a thermistor and converts the measurement to digital temperature data). This temperature data can be provided to the processor 60 that uses the measured temperature to adjust the heater 68 so as to achieve a target temperature. Such target temperature is most often, but not necessarily, about 37° C.±approximately 2°-3° C. In one implementation, the actual gas temperature can be sent from the blender controller 60 via communication bus 38 to the processor 26 of the adaptive controller 18 to be displayed on, e.g., a three digit display forming a part of the user interface 30. In other embodiments, a display forming a part of user interface 30 can be realized as a touch screen display or other display that is utilized to display any desired set of operational parameters of the system and measurements from the patient. Further, the user interface 30 may include virtual and/or actual buttons and indicators as well as other controls for use by medical personnel to enter data and provide directives for prescribed delivery of therapeutic gas blends for inspiration by the patient 10, setting alarm limits, etc.

The system 34 may also provide for measurement of at gas flow rate and/or pressure at 80 with such measurement being provided to and controlled by the processor 60. Processor 60 can further provide the pressure and/or flow rate information as well as other operational parameters and alarms via bus 38 to processor 26 for display to medical personnel on user interface 30. Control of the flow rate and pressure of the gases can be implemented by controller 60 by use of valves at the oxygen mixer 64 (or elsewhere).

Additionally, the processors 60 and 30 can compare various measured data with a set of prescribed alarm limits (either pre-configured or set by input by medical personnel) which will cause alarms to be generated (i.e., audible and visual alarms, or signals that can be monitored remotely—such as at a nurse's station), shown as 84.

Hence, the present adaptive controller system 18 uses input signals of a patient's blood oxygen levels, as assessed by the pulse oximeter, to calculate the appropriate oxygen level for delivery to the patient by the blender system 34. The adaptive controller processor 26 continuously monitors the patient's blood oxygen and provides oxygen level adjustment at regular intervals, e.g., approximately every 10 seconds. PID control is used in this example embodiment as a mechanism to adaptively adjust the oxygen levels to the needs of the patient as assessed by the pulse oximeter.

In the present system, under most conditions, the overall system control is handled by controller 26 operating as a master controller. However, the delivery of gasses to the patient can be controlled by either the adaptive controller system in an adaptive mode or can be overridden by a manual mode implemented by control of either the adaptive controller system 18 or by the blender system 34. For example, at times, the blender system 34 send signals to the adaptive controller system 18 directing an operational mode change, such as from automatic to manual adjustment of oxygen levels. So, for example, if medical personnel take an action at the blender system 34 to take over control of the gas blend or other operation of the blender system manually, the blender controller 60 detects this action and instructs the processor 26 to relinquish control over the gas mixture to a manual override controlled at the blender system.

In accord with the present teachings, processor 26 may be one or more programmed processors programmed in any one or more suitable languages such as C, C++, Perl, etc., as well as other adjunct languages where desirable. The processor 26 can be implemented using, for example, industry standard processors such as the Atmel ARM-based processors such as the SAM9263 series microcontroller (e.g., the AT91SAM92638) running the GNU/Linux operating system. The above constraints are not to be considered limiting since other configurations can also be utilized.

In systems consistent with the present teachings, it certain default settings can be provided to establish a baseline operation in the absence of overriding instructions from medical personnel. Such default settings can be stored at 28. In one example embodiment, the following illustrative non-limiting default settings of TABLE 1 can be established:

TABLE 1

| PARAMETER | DEFAULT VALUE |
|---|---|
| Pause time | 1 minute |
| Default pulse oximeter cable connection type | Masimo ™ |
| Default operational mode of Blender System | Blend Mode |
| Default $O_2$ mixture for delivery to patient | 35% |
| Default airway connection | Nasal Cannula |
| $O_2$ Maximum Alarm | 60% |
| $O_2$ Minimum Alarm | 21% |
| $O_2$ Limit Alarm | 60% |
| Pulse Rate Minimum Alarm | 80 bpm |
| Pulse Rate Maximum Alarm | 180 bpm |

BLEND MODE/SMART MODE (AND OTHER MODES)—There are two (2) modes of operation in the present implementation: BLEND and SMART. Blend mode is "manual" mode of operation where the end-user makes manual adjustments of oxygen percentage. Smart mode is where the computer makes adaptive adjustments of oxygen percentage. Other modes of operation may be devised without limitation Possible airway connection settings Nasal cannula. The default setting for airway connector is NASAL CANNULA. Other options of airway connectors include MASK in which a mask is used. When used with invasive systems or other airway connectors, other connection settings can be provided for.

$O_2$ max and min—The preset values of oxygen limits are 21% and 60%. The lowest value is 21% but the upper value can be set as high as about 80% in this implementation.

Pulse rate max and min—The preset values of pulse rate are 80 bpm and 180 bpm in this implementation. These values can be adjust up of down by the end-user.

Upper $O_2$ limit—This LIMIT is a safety feature of the device. The preset limit is 60% $O_2$ in the present embodiment and can be adjusted by the end-user. The $O_2$ Maximum Alarm can be set above or below this LIMIT.

Other alarm limits can also be established such as interface type, flow rate, temperature, humidity, manual override status, etc.

In this example, the pause time is the default amount of time that the microprocessor uses to indicate an internal problem or fault that is detected at startup and during operation. The Pause Time is the time used by a watchdog timer to determine that the system has locked up during boot or has otherwise malfunctioned during operation (e.g., stuck in a loop or other error has occurred that interferes with normal system operation). When this pause time expires it is indicative that the system has detected a failure and a critical alarm is issued.

The Operational mode of the blender system can be Blend Mode in which the air and oxygen are blended. 100% oxygen is delivered and mixed with 21% Air. The default $O_2$ mixture of 35% is the default setting in certain embodiments for the blender to produce in the absence of another setting. The default airway connection is Nasal Cannula, which the user can override with settings such as Mask or Endotracheal. The $O_2$ maximum alarm limit sets an alarm when the $O_2$ level being delivered exceeds a defined limit. The $O_2$ minimum alarm limit sets an alarm when the $O_2$ level falls below a prescribed limit. The Upper $O_2$ alarm limit is a safety feature to ensure that oxygen does not rise above the preset value of 60%. The minimum and maximum pulse limits define a range of pulse rates allowable with an alarm being produced if those minimum and maximum values are breeched.

Alarm 34 may provide any of several alarm conditions, as will be explained later. Briefly, a cautionary audible alarm signal may include (e.g., an audible tone, beep, buzz, voice or the like). In one example embodiment, the processor 26 controls the alarm to produce an audible signal with a sound pressure level that is within, for example, about ±3 dB of an Emergency Alarm Audible Tone measured at the point 1 meter from the user interface of adaptive controller system 18. The Emergency Alarm Audible Tone, is similarly controlled by the processor 26 to produce an output audible alarm signal that has a sound pressure level of 70 dB+/−10 dB measured at the point 1 meter from the adaptive controller system 18.

In certain example embodiments, the user interface 30 provides for input of data that can be stored at 28 including, for example the data shown on the following TABLE 2:

TABLE 2

| INPUT | FUNCTION |
| --- | --- |
| Power Button | This button is used to turns the Adaptive Controller System on and off |
| StandBy Button | Puts the Adaptive Controller System into manual adjustment mode |
| Smart Button | Puts the Adaptive Controller System into computer adjustment mode |
| Initial $O_2$ Button | Sets initial $O_2$ level - overrides default |
| $O_2$ Upper Limit Button | Set upper limit of $O_2$ level - overrides default |
| $SpO_2$ Upper Alarm | Set upper $SpO_2$ alarm - overrides default |
| $SpO_2$ Lower Alarm | Sets lower $SpO_2$ alarm - overrides default |
| Pulse Rate Upper Alarm | Set upper pulse rate alarm - overrides default |
| Pulse rate Lower Alarm | Sets lower pulse rate alarm - overrides default |
| Trend Time | Used to set a Trend Time frame which provides a graphical representation of alarms, alarm conditions, $O_2$ level, $SpO_2$, oxygen delivered, pulse rate, etc. |
| $O_2$ Increase Button | Incrementally increase $O_2$ level |
| $O_2$ Decrease Button | Incrementally decrease $O_2$ level |
| Time/Date | Allows entry of a new Time or Date |
| Patient Data | Allows entry of patient data |

The user interface 30 can further provide display visual indicators and data that are useful to the medical personnel in treating patient 10. Such displayed information may, for example include some or all of the data of TABLE 3 as well as other data that may be deemed useful without limitation:

TABLE 3

| DISPLAY | FUNCTION |
| --- | --- |
| Power Button Indicator | Indicates position and availability of Power Button (note - not always available for safety considerations) |
| Operational Mode | Indicates mode of delivery of gas |
| $O_2$ display | Indicator of $O_2$ level delivered by Blender system |
| $SpO_2$ Display | Indicator of $SpO_2$ level assessed by pulse oximeter |
| Pulse Rate Display | Indicator of pulse rate level assessed by pulse oximeter |
| StandBy Display | Indicates if Adaptive Controller System is in manual mode |
| Smart Display | Indicates if Adaptive Controller System is in in computer mode |
| Trend Time | Indicates trend time-frame |
| $O_2$ Upper Limit Alarm | Indicates when $O_2$ exceeds upper limit |
| $SpO_2$ Alarm | Indicates when $SpO_2$ has exceeded upper or lower limits |
| Pulse Rate Alarm | Indicated when pulse rate has exceeded upper or lower limits |
| Low Perfusion Alarm | Indicated when $SpO_2$ value is not reliable |
| Sensor Off Patient Alarm | Indicated when $SpO_2$ sensor disconnects from patient |
| Sensor Disconnect Alarm | Indicated when $SpO_2$ sensor disconnects from Adaptive Controller System |
| Patient Data | Name and other identifiers for patient |
| Gas Temperature | Indicates Temperature of inspired gas (from Blender System) |
| Gas Humidity | Indicates Humidity of inspired gas (from Blender System) |
| Gas Flow Rate | Indicates flow rate of inspired gas (from Blender System) |

FIG. 2 depicts one simplified non-limiting example of a collection of data displayed in an illustrative user interface display 30.

Figure 3:
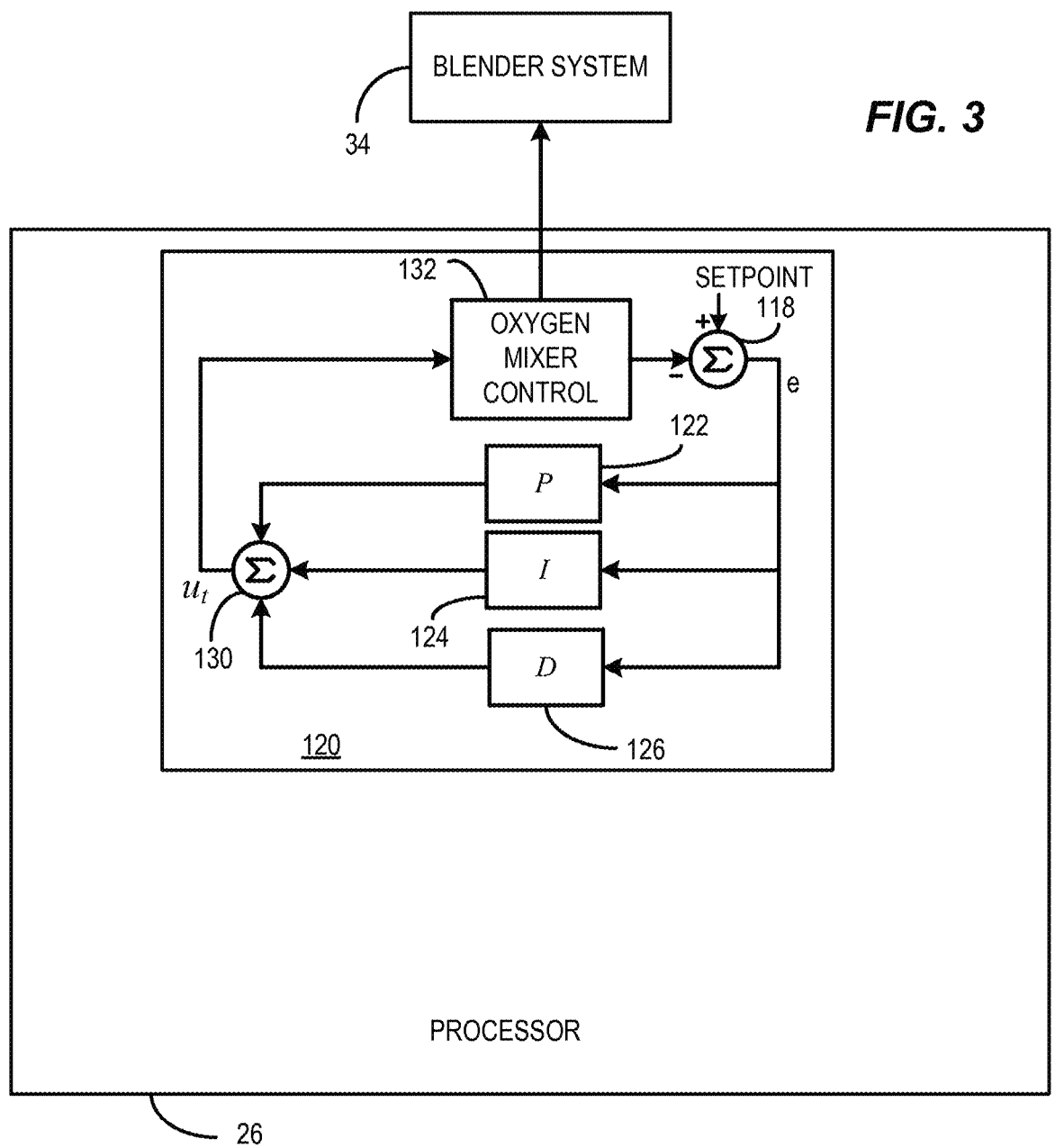
FIG. 3 is a block diagram of an example PID controller system consistent with certain example embodiments of the present invention.

FIG. 3 shows one non-limiting example of a PID controller 120 as can be implemented in processor 26 and used in certain implementations to control oxygen mixer 64. In other example implementations, a PI controller (Proportional Integral) or other suitable feedback controller could alternatively be used. The proportional-integral-derivative controller (PID controller) 120 is a control loop feedback controller that calculates an error value as the difference between a measured process variable and a desired value of the process variable (or set point). The controller operates to minimize the difference between a measured value and the set point. A PID controller accomplishes this by use of an algorithm that uses three separate parameters—proportional (P), integral (I) and derivative (D) values interpreted at discrete increments of time where P depends on the current error, I depends of the accumulation of past errors, and D predicts future errors. The weighted sum of these three actions is used to adjust a process—in this case the proportion of oxygen represented by $FiO_2$.

In FIG. 3, when a conventional PID controller is used and when all three functions P 122, I 124 and D 126 are utilized, the values of P, I and D are given by:

$$P = K_p \varepsilon(t) \qquad \text{(Eqn. 1)}$$

$$I = K_i \int_0^t e(\tau) d\tau \qquad \text{(Eqn. 2)}$$

$$D - K_d \frac{de(t)}{dt} \qquad \text{(Eqn. 3)}$$

where the oxygen mixer control signal is derived from the PID controller output from adder 130 represented as $u_t$:

$$u_t = P + I + D = K_p e(t) + K_i \int_0^t e(t) dt + K_d \frac{de(t)}{dt} \qquad \text{(Eqn. 4)}$$

and where:
$K_p$: Proportional gain coefficient;
$K_c$: Integral gain coefficient;
$K_d$: Derivative gain coefficient;
e: Error, difference between measured and target;
T: Time; and
$\tau$: Integration variable; takes on values from time 0 to present time t.

The current value of $PaO_2$ (representing the measured $SpO_2$ as will be discussed later) is subtracted from the setpoint (i.e., the target value) at 118 to produce the error signal e at the output of 118. This error signal is then processed by the P, I and D blocks 122, 124 and 126 respectively according to the equations above. The outputs of blocks 122, 124 and 126 are summed at 130 to produce $u_t$ which is provided to the oxygen mixer control 132. The value control signal is put into an appropriate format by oxygen mixer control 132 of processor 26 and output to the blender controller 60 of blender system 34. This information is then used by the blender controller 60 to effect control of the oxygen mixer 64 to establish the appropriate blend of gasses dictated by the PID controller.

For the present embodiment, the PID controller equation being used is:

$$PaO_2 = (KL * FiO_2) + K2, \qquad \text{(Eqn. 5)}$$

where KL is the lung function gain coefficient relating the lung's ability to efficiently transfer oxygen and carbon dioxide. K2 is the offset relating to level of over-all respiratory capability.

This equation is based upon a PID controller equation from Sano and Kikuchi, IEE Proceedings, Vol. 132, Pt. D, No. 5, Sep. 1985 which is hereby incorporated by reference and which had an offset (K2). This offset has been found to be approximately zero and is negligible in the present embodiment. Hence, K2 has been dropped due to the system working on the dissociation curve greater than 85%. Accordingly, this equation has been modified for the present application by dropping the constant K2 for use with the present PID controller. Also, this PID controller uses a relatively long sample period of about 10 seconds which serves as a type of low-pass filter to ensure accuracy of $SpO_2$ calculated from the $SpO_2$ monitor.

Another type of low-pass filter can be provided by using, for example, 90% of old data (from prior sample period) and adding in, for example, 10% of the new data (from new sample period). Both of these filters enhance the system performance so it is more responsive but not overly responsive.

Another feature of the present example embodiment of the PID controller is the "initial" value of $O_2$ used by the system upon initiation of the adaptive process. The initial value is set by the end-user and is used by the PID controller to ensure the system starts in a relatively steady-state condition. It is generally undesirable to have the PID controller adjusting the $O_2$ level up and down upon start-up so as to find a steady-state. The end-user's input of $O_2$ helps mitigate this up and down operation at startup.

It is further noted that linear interpolation of $SpO_2$ to $PaO_2$ usually adequately accounts for pH, Temp, and DPG. The patients using this system are often in managed care or in a step-down environment. So assuming the above three (3) factors are not significant issues, pH and Temperature can be assumed to be stable. DPG is usually "washed-out" of the newborn's blood within 72 hours after birth.

The system is initialized to ensure that the system starts operation in a steady-state condition. An initial KL is calculated by:

$$KLi = PaO_2i/FiO_2i, \quad \text{(Eqn. 5)}$$

where KLi, $PaO_2i$, and $FiO_2i$ are all initial values.

Furthermore, within each sample period of the PID controller, an adaptation algorithm uses a calculation to form new PID gain coefficients. The algorithm used in the present implementation is given as:

$$(\text{new})KL = 0.9(\text{old})KL + 0.1(PaO_2/FiO_2), \quad \text{(Eqn. 6)}$$

where the (new) KL is used for calculating (new) PID gain coefficients.

Figure 4:
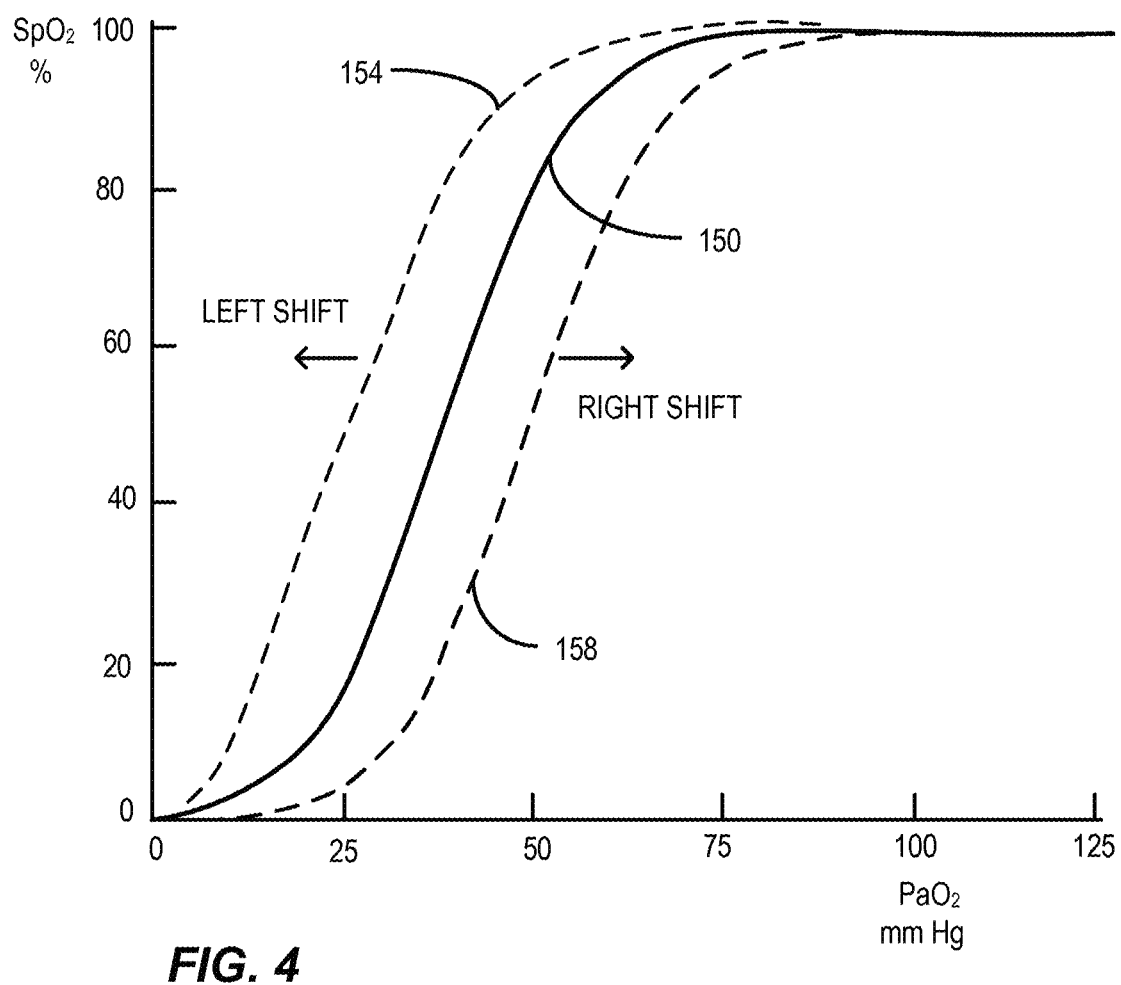
FIG. 4 is a graph depicting an approximation of an oxyhemoglobin dissociation curve consistent with use in certain example embodiments of the present invention.

In the process described above, the value of $SpO_2$ is measured and converted to a value of $PaO_2$ for use by the PID controller for its calculations. This conversion can be effected in a number of ways. With reference to FIG. 4, in one example embodiment consistent with the present invention, the $SpO_2$ measurement as acquired by the pulse oximeter is converted into the correlating partial pressure of atrial oxygen ($PaO_2$). This is done in the present embodiment because of the relationship between $PaO_2$ and control of the example oxygen mixer 64, but in other embodiments control signals for the oxygen mixer can be more directly derived from $SpO_2$ or other measures of a patient's blood oxygen concentration without limitation.

Conversion from $SpO_2$ to $PaO_2$ can be accomplished in a variety of ways. Conventionally, medical personnel may utilize an oxyhemoglobin dissociation curve to obtain $PaO_2$ from $SpO_2$ under standard conditions of Temperature=37° C., PH 7.4, and BE=0. An example approximation of an oxyhemoglobin dissociation curve is shown as 150 of FIG. 4. This curve is an approximation used for illustration in this document only and is not to be used for treatment of a patient. In this illustrative curve, if one knows the value of $SpO_2$, the value of $PaO_2$ can be read from the graph. However, the relationship becomes somewhat difficult to interpret at high levels of $SpO_2$. Additionally, the curve can shift left as depicted by dashed curve 154 or shift right as depicted by dashed curve 158. Shifting of the curve to the left represents conditions causing high $O_2$ affinity. Shifting of the curve to the right represents conditions causing low $O_2$ affinity.

The curve 150 approximates a sigmoidal shape and various equations can be devised to closely model the shape of the curve using various curve fitting techniques. With such an equation, the value of $PaO_2$ can be computed directly. However, such computation is complex and computationally intensive. In certain example embodiments, data points from this curve can be cataloged into a lookup table stored in storage and/or memory 28 which can be used to convert the value of $SpO_2$ to a value of $PaO_2$. This can be done to any desired degree of accuracy for use as a lookup table.

Under the above standard conditions, the relationship between $SpO_2$ and $PaO_2$ can be approximated by a lookup table such as the partial lookup table shown in TABLE 4 below:

TABLE 4

| $SpO_2$ | $PaO_2$ | $SpO_2$ | $PaO_2$ |
|---|---|---|---|
| 10 | 10 | 88 | 55 |
| 30 | 19 | 89 | 57 |
| 40 | 23 | 90 | 60 |
| 50 | 26.5 | 91 | 62 |
| 60 | 32 | 92 | 65 |
| 70 | 37 | 93 | 69 |
| 80 | 44.4 | 94 | 73 |
| 81 | 45 | 95 | 79 |
| 82 | 46 | 96 | 86 |
| 83 | 47 | 97 | 96 |
| 84 | 49 | 97.5 | 100 |
| 85 | 50 | 98 | 112 |
| 86 | 52 | 99 | 145 |
| 87 | 53 | 99.75 | 700 |

This lookup table is again for illustrative purposes only and not intended for the treatment of any patient. In certain example implementations, the above TABLE 4 (or a more complete and more precise table) can be used to translate $SpO_2$ to $PaO_2$ by first doing a look-up of the value of $SpO_2$ and then, if the exact value is not on the table, doing a linear or non-linear interpolation or any suitable interpolation (e.g., polynomial, piecewise constant interpolation, spline interpolation, bilinear interpolation, extrapolation, etc.). Using linear interpolation by way of example, if the $SpO_2$ value is 91.6, the $PaO_2$ value can approximated by using a linear interpolation to be approximately:

$$PaO_2 = (91.6 - 91)/(92 - 91) \times (65 - 62) + 62 = 63.8.$$

The more data points provided in the lookup table, the more accurate an interpolation, if necessary, will be. It is noted that the above TABLE 4 is presented by way of example and is only approximately accurate under standard conditions discussed above. The example lookup table is small and may result in undesirable accuracies, but is presented for ease of illustration of the principles involved. It is again noted that neither the curves of FIG. 4 nor the data of TABLE 4 should be used for actual medical purposes. This data is only provided for purposes of illustration. Accurate medical references should be used for actual patient treatment purposes.

Figure 5:
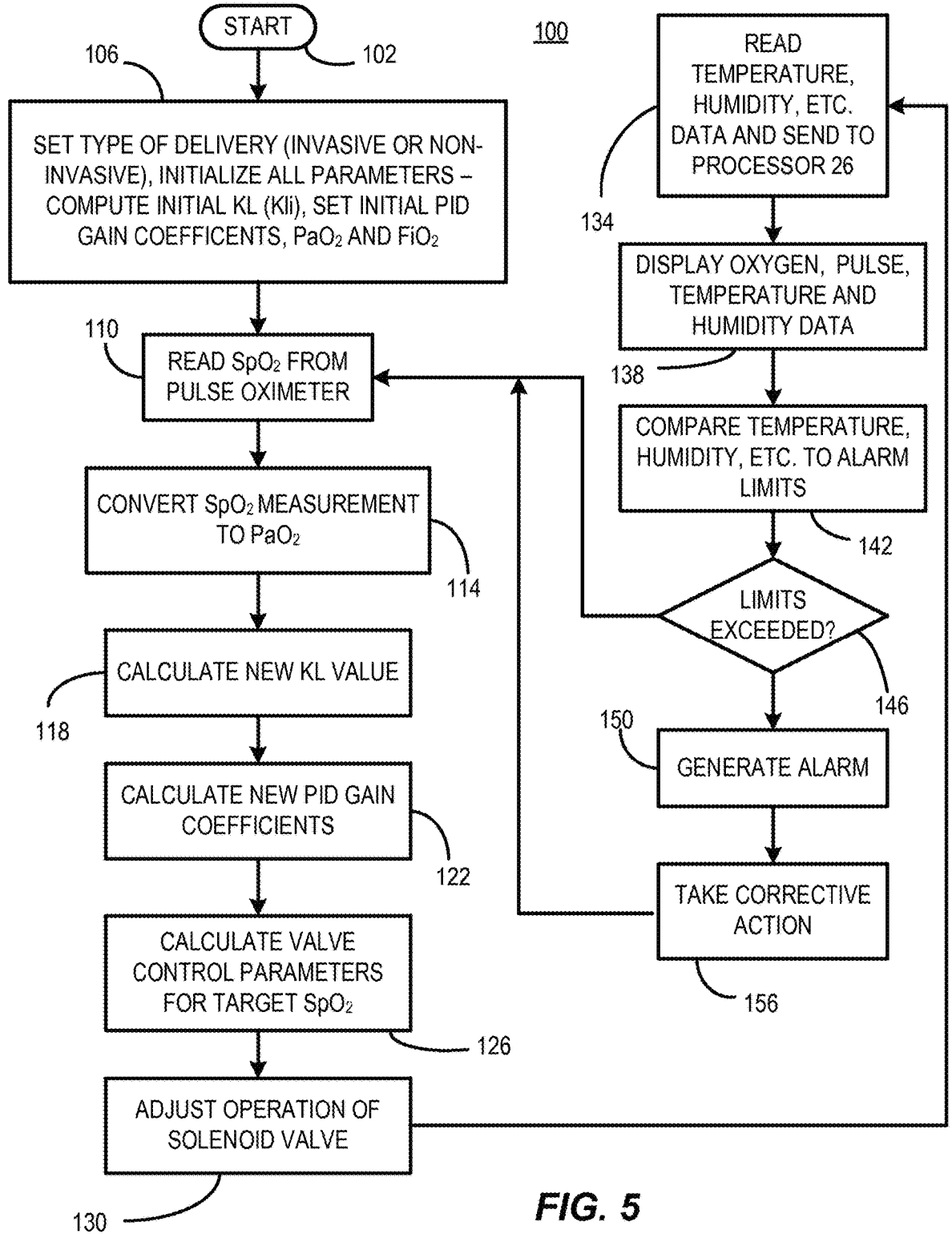
FIG. 5 is an example flow chart of overall operation of an illustrative system consistent with certain example embodiments of the present invention.

Referring now to FIG. 5, an illustrative flow chart 200 depicting an overall mode of operation of certain implementations is depicted starting at 202. At 206, the system is initialized with all relevant parameters including PID controller gain coefficients, and the medical staff inputs type of delivery (active or passive; i.e., invasive or non-invasive) along with other relevant data including patient information. At 210, the $SpO_2$ reading is taken from the pulse oximeter and this measurement is converted to $PaO_2$ at 214. A new value of KL can then be computed at 218 and new PID controller gain coefficients can be calculated at 222. This calculation results in determination of parameters that can be used by the blender controller to calculate valve control parameters to obtain the target $SpO_2$ as computed by the processor 26 at 226. Accordingly, the valves of oxygen mixer 64 can be adjusted by blender controller 60 to achieve the desired gas mixture at 230.

At 234, the blender controller reads various data generated in the blender system 34 such as temperature, humidity, pressure, gas flow, etc. and sends that data to processor 26 of the adaptive controller system 18 via bus 38. The processor 26 then sends the data from the blender system 34 as well as internally generated data to a display forming a part of user interface 30 for reading and interpretation by medical personnel at 238. Processor 26 also compares the data sent by the blender system with established default or operator set alarm limits at 242. If any alarm limits are exceeded at 246, an alarm 84 is generated at 250 to alert medical personnel that there is a potential problem. For example, if the processor detects that the patient's $SpO_2$ level is below a threshold (e.g., 90%), an alarm may sound to alert medical personnel that there may be either a degradation of the patient's condition or there may be a malfunction. In another example, if the temperature of the inspired gas mixture is detected to be greater than an upper limit (e.g., 40° C.), then an alert may be generated to let the medical personnel know that there is a potential problem.

Additionally, in certain cases, where possible, the adaptive controller system 18 may take certain corrective actions at 254 when an alarm limit is exceeded. In one example, if the alarm limit is exceeded for the lower limit of $SpO_2$, the adaptive controller processor 26 may, for example, cease to provide adaptive control over the gas mixture. Additionally, the control processor may set a prescribed or default oxygen mixture (e.g. 60%) or at the most recent oxygen mixture to be delivered by the blender system 34 and revert the blender system to manual control while sounding an audible alarm and providing a visual indication of the situation and actions taken. Other actions are possible without departing from the present teachings.

FIG. 5 depicted a simplified example process that illustrates the overall operation of the system 26. Referring now to FIG. 6A-6I, starting at FIG. 6A, an example process 200 is depicted for operation of the adaptive controller system as described herein in flow chart form. The processes depicted are carried out in certain implementations utilizing processor 26 to control the adaptive controller system 18. Such processor may be realized as a hard wired processor or as a programmed microcontroller or the like that includes or is connected to non-transitory memory devices that store instructions that when executed on the processor 26 (which may also be realized as multiple processors) cause the processes described to be carried out. The system includes program memory (not shown explicitly), with unused locations of the program memory being set to an instruction that will cause the processor to go to a known safe state if executed.

The system 18 operates in a number of defined functional states, some of which are states which are continually passed through in order to carry out certain monitoring and alarm functions. The process begins at 202 after which at 206, if the system is not turned on, the only function is retention of non-volatile memory contents that stores non-volatile data.

When the system 26 is turned on at 206, a booting and initialization process is carried out at 214 wherein program instructions are loaded, initial checks are carried out and so forth. The power on/standby state is entered at 218 at which point a standby button or other indicator is illuminated and a smart button (indicating operation of the system 26 in adaptive control mode) and illumination associated therewith is disabled. This state is entered when power is first applied to the controller or after an emergency alarm or after a manual change in oxygen level of the blender system 34.

At 222, regardless of the state of the system 18, editing of time, date, patient data, gas mixture delivery mode, network link system tests and download of data to external storage or to remote monitoring stations (not shown) is permitted. At 226, the system action is determined by the state or states that are currently active. It is noted that certain states may be active at all times, while others are only active upon user control or under alarm conditions, etc. However, depiction of the system operation as a collection of states is a convenient mechanism to convey the operation of the present illustrative example embodiment.

Figure 6A:
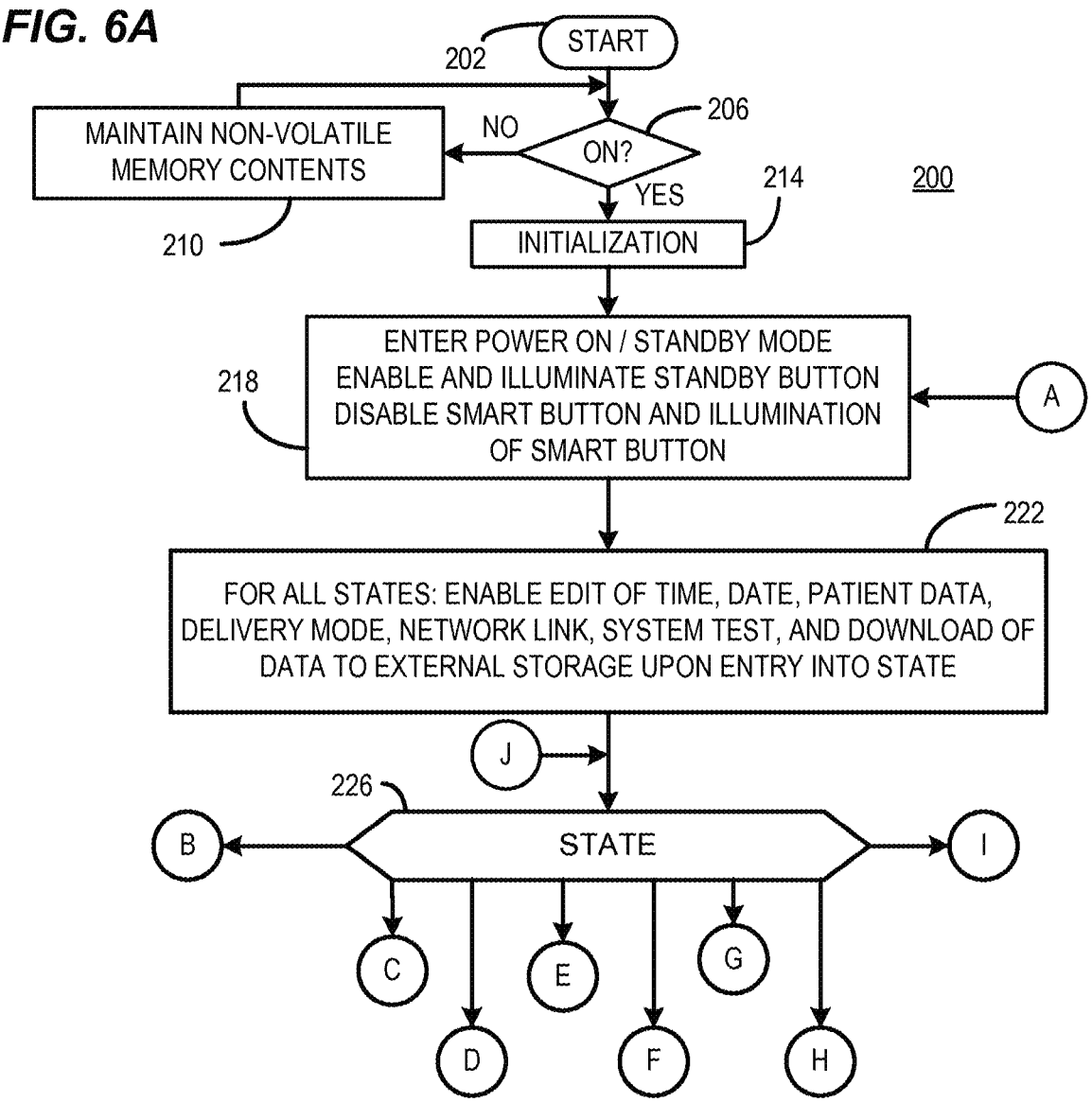
FIGS. 6A through 6I depict a flow chart of an example operational process consistent with certain example embodiments of the present invention.
Figure 6B:
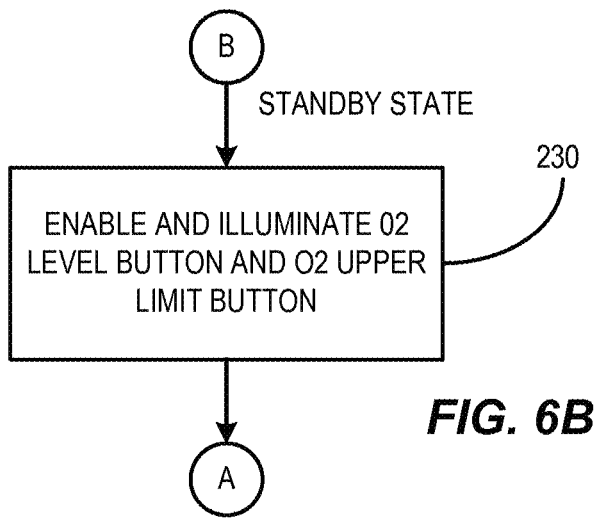

When the system is in the standby state, various measurements can be displayed in certain implementations. With reference to FIG. 6B, when the standby state is entered at 230, the $O_2$ level and upper limit button are illuminated and adjustment of associated parameters is permitted.

Figure 6C:
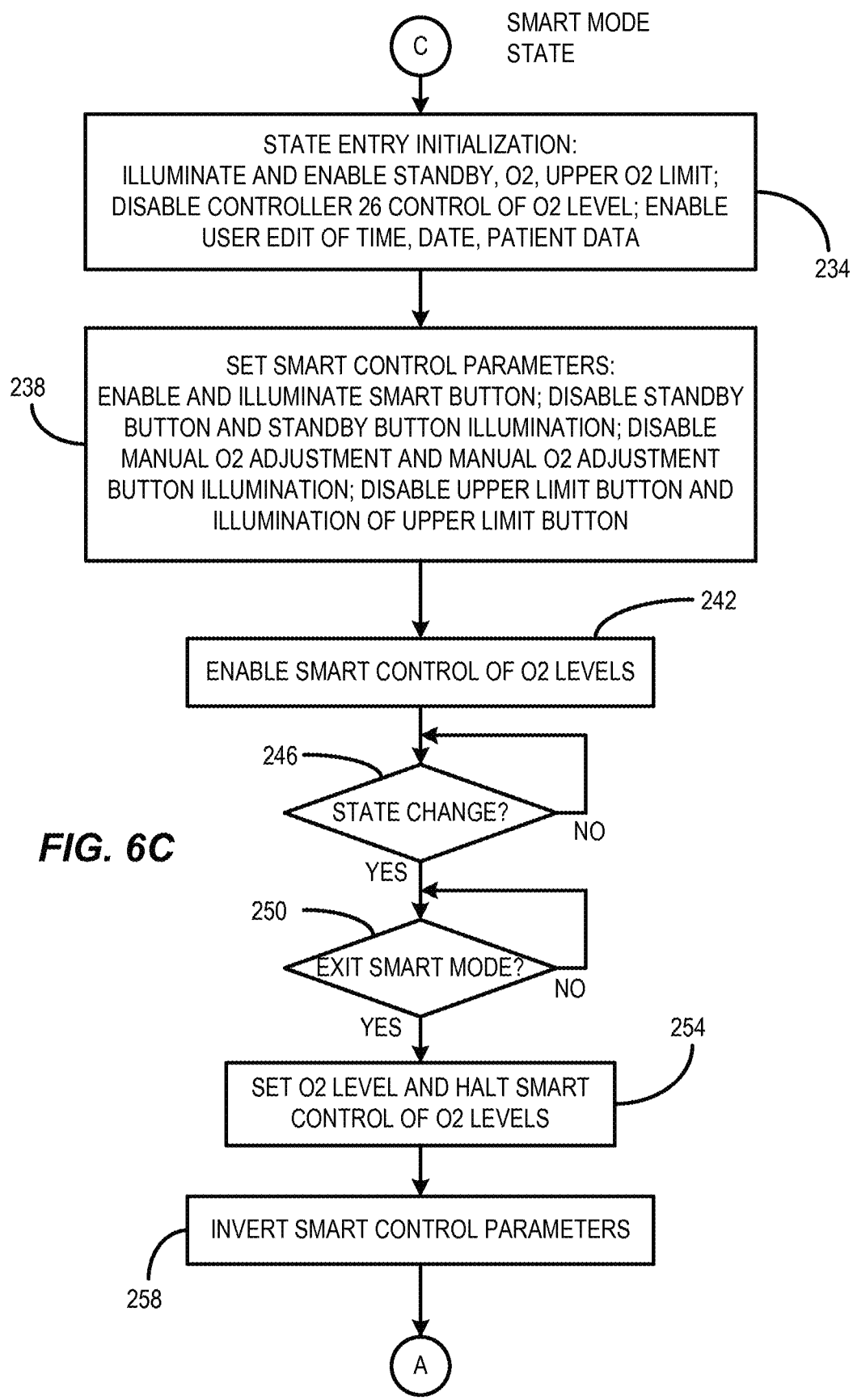
Figure 6D:
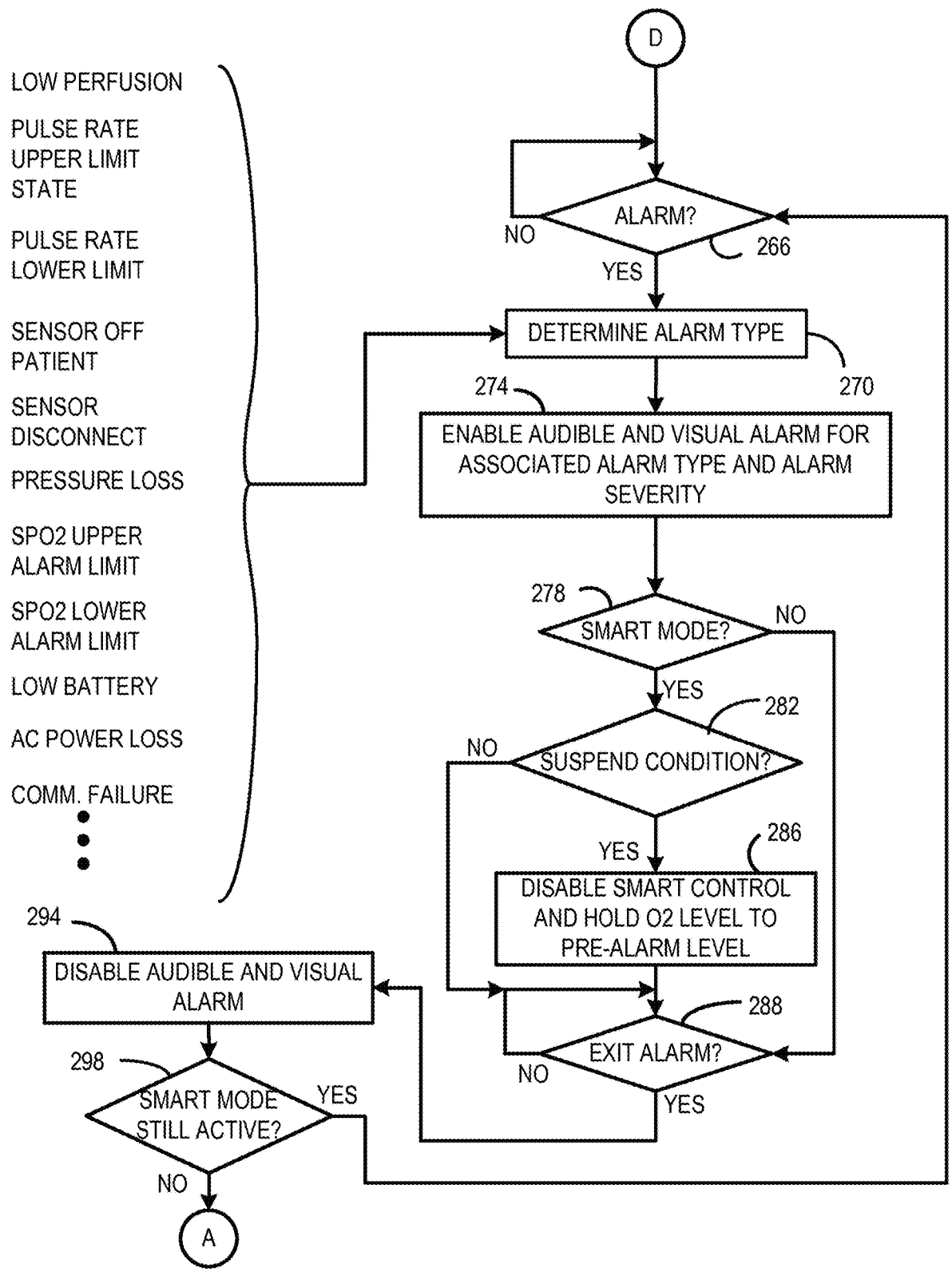

Referring to FIG. 6C, the general operation of the system 18 when in the "smart" mode state is depicted. In this state, the system 18 is operating to carry out adaptive control of the gas mixture produced by blender system 34 using the PID control mechanism or other suitable mechanism as describe previously. Upon entering this state at 234, the standby, $O_2$ level, $O_2$ upper and lower limits are illuminated and enabled. Controller 26 is initially disabled while editing an entry of patient, time, date and other parameters are entered.

At 238, the smart control parameters are set and the smart control enable button is illuminated and enabled. The standby button and illumination are disabled as are the manual $O_2$ adjustment button and illumination thereof, and the upper limit button and illumination thereof. Smart (adaptive) control of the gas mixture is then commenced at 242 in order to utilize the $SpO_2$ feedback PID control of the gas mixture to achieve a target peripheral blood oxygen level as measured by the pulse oximeter 12.

If a state change is detected at 246, and if such state change dictates, the smart mode may be exited at 250. Whenever a state change occurs that dictates exiting the smart mode, a provision is made at 254 to continue to supply a blend of gasses to the patient 10. In the present example, the gas mixture is set at the last setting dictated by the adaptive control system 18. In other examples, the $O_2$ level could be set for another value including increased or decreased oxygen levels or a predefined default level without limitation. When the smart mode is exited, the medical personnel are notified by an alarm so that manual control can be instituted based upon the patient's condition. At 258, the smart control parameters set at 238 are inverted and the system 18 enters the standby mode at 218. Smart mode operation is not reentered until the medical personnel take steps to re-activate the smart mode.

There are multiple events that can trigger one or more of multiple types of alarms depending upon the severity of the alarm condition. The operation of the alarms states is depicted in the example process of FIG. 6D starting at 266 where alarm conditions are monitored and alarm conditions are detected. When an alarm is detected at 266, the type of alarm is determined based upon the input received by the processor 26. Several examples of alarm conditions include, but are not limited to: low perfusion, pulse rate limits exceeded, sensor off patient or disconnected, pressure loss, $SpO_2$ upper or lower limits exceeded, low battery, AC power loss, inspired gas temperature or humidity outside limits, flow rate limits exceeded, blender system alarms, etc. When an alarm condition exists, the type and severity of the alarm are determined at 270.

Some alarms may only be deemed by the system 18 to be issues that should be monitored. For example, a slight deviation in gas humidity or a low battery when operating on AC power may not be an emergency, but should be brought to the attention of the medical personnel. Other alerts such as a loss of pulse or $SpO_2$ readings are deemed unreliable may be deemed an emergency condition. In any case, at 274, an audible and/or visual alarm is produced according to the type and severity of the alarm state. The types of alarm conditions will be discussed later.

At 278, if the system 18 is operating in smart mode and thus adaptively controlling the gas mixture, and if the alarm is of such nature that adaptive control is deemed inappropriate at 282, the smart mode is disabled at 286 and the gas mixture level is set to the latest pre-alarm level so that medical personnel can make adjustments manually.

If the alarm is such that the adaptive control (smart mode) can be maintained at 278, then 282 and 286 are bypassed and the smart mode continues. From 286 (or 282 or 278 if the alarm does not interrupt smart mode operation), control passes to 288 where if the alarm state is resolved, then the audible and visual alarms are disabled at 294. If the smart mode is still active at 298, control returns to 266 to await and monitor for another alarm condition. If the smart mode has been disabled at 286 as determined at 298 (for example in the case of an alarm indicating that the measured oxygen levels are not reliable), then the system enters the standby state at 218 until operation of the adaptive control is resumed under operator control.

Figure 6E:
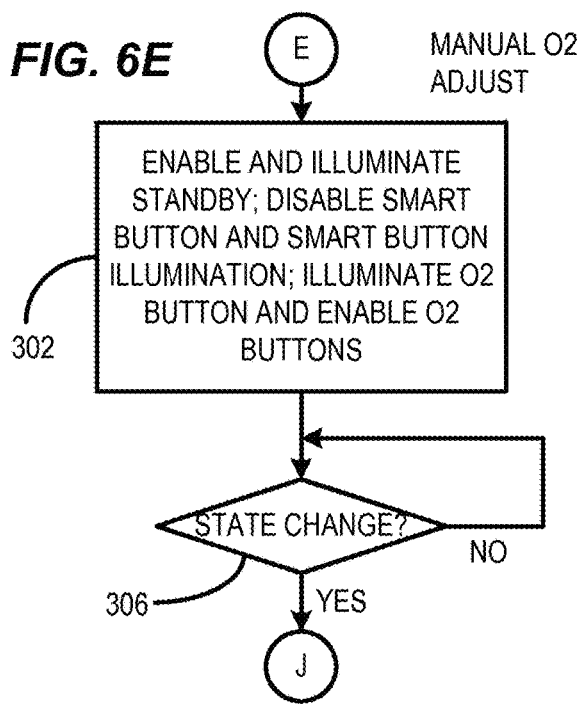

An example manual adjustment state is depicted in FIG. 6E. In this state, the system is in standby mode at 302 and the standby button is illuminated. The smart mode is disabled and the $O_2$ enable button is enabled and illuminated. The system 16 remains in standby until such time as there is a state change that, for example, takes the system into smart mode at 306. Control then passes to 226.

Figure 6F:
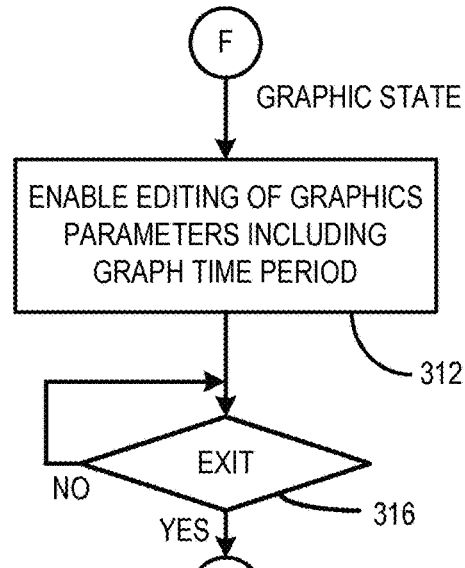

An example of the graphic state is depicted in FIG. 6F. In this state, the operator is able to edit graphics parameters at 312 for graphical data that can be displayed, stored or printed from the system 18. An example is a time period for the graphic display. Such graphic display can present trend data and other information to the medical personnel that are indicative of the patient 10's progress and trends, for example. In one example, the data can represent $SpO_2$ over, pulse or gas temperature a selected time period. Those skilled in the art will appreciate that other graphical values can also be presented upon consideration of the present teachings. This state is maintained until exited at 316 by user control or, for example, by time out.

Figure 6G:
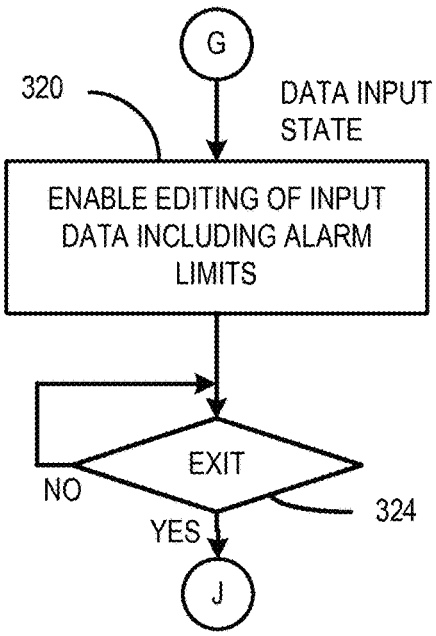

FIG. 6G represents an example of operation of system 18 in a data input state. In this state, the system 18 permits input at 320 of alarm limits and other data that may set system operational parameters. This state is maintained until exited at 324 by user control or, for example, by time out.

Figure 6H:
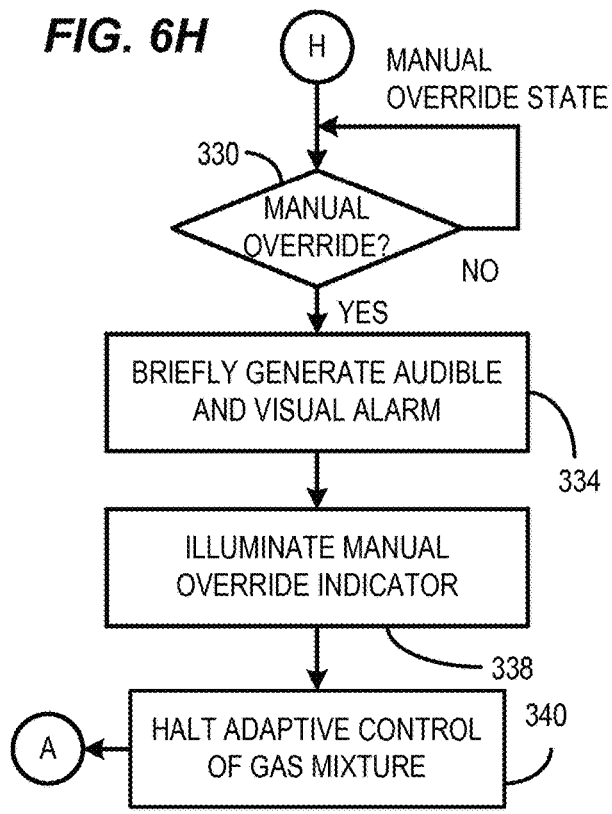

FIG. 6H represents an example state of operation of system 18 in which a signal indicating that a manual override has been initiated at the blender system 34. This signal is detected by the processor 26 as a result of a message from blender controller 60 at 330. In response thereto, the system 18 generates a brief audible and visual alarm at 334 (a cautionary alarm) and a manual override indicator is illuminated at 338. The system 18 then halts adaptive control of the gas mixture at 340 and enters the standby mode until the smart mode is reactivated by operator control. Manual override may be engaged by, for example, user adjustment of a gas mixture at the blender system 34 or by a control at interface 30. When this occurs, the occurrence of this event is conveyed from the blender system 34 to the adaptive controller system 18 via 38.

Figure 6I:
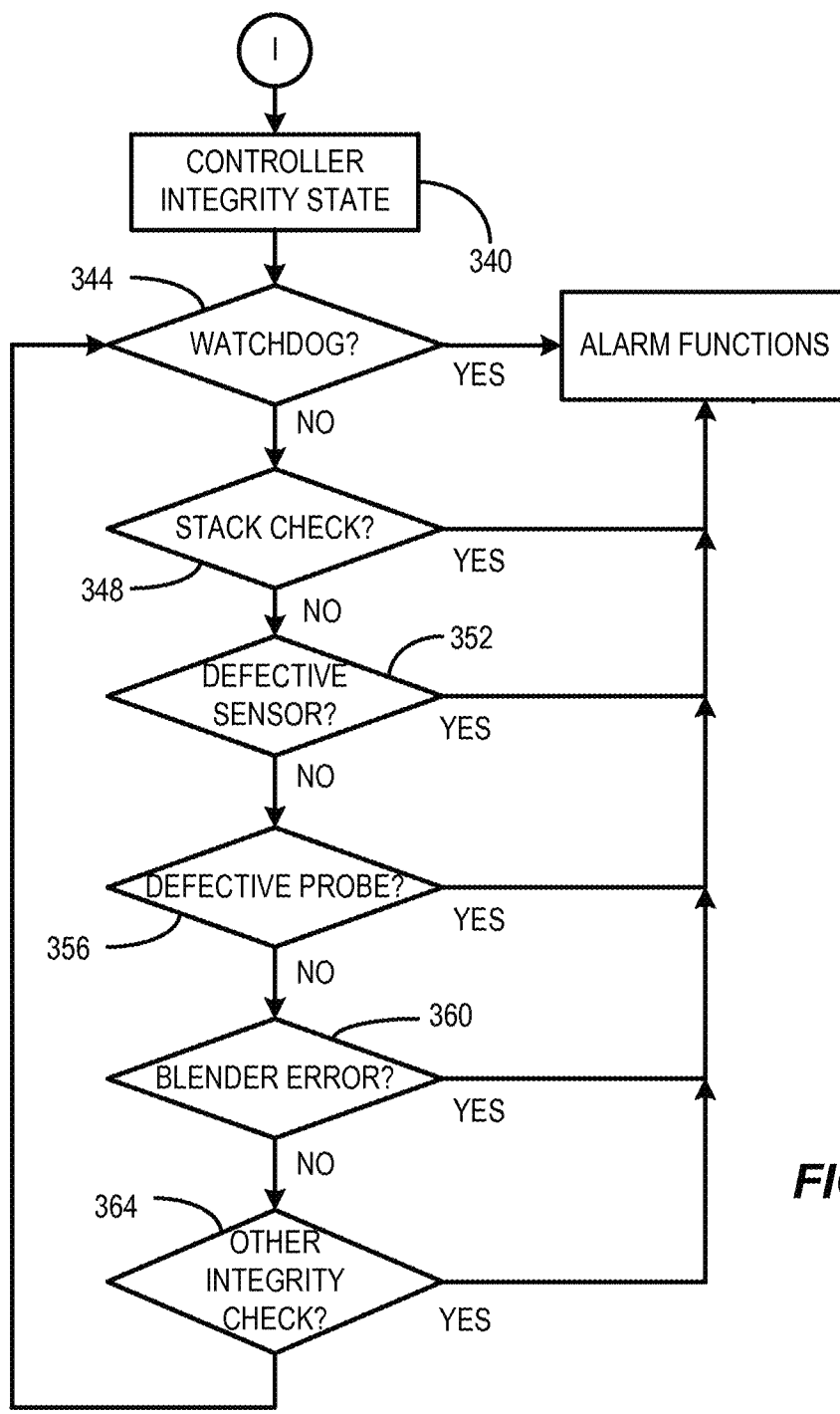

System 18 is also configured to carry out multiple system integrity tests on a periodic and/or ongoing basis in order to assure proper operation of system 18. FIG. 6I depicts an example of several integrity tests that may be carried out in accord with the present teachings starting at 340.

At 344, the system can carry out a watchdog check in which critical areas of functionality are examined to determine if the functions are operating as designed and as expected. A check of data memory stacks is carried out at 348 to determine if a stack overflow or underflow has occurred. At 352 a check is made to determine if the system has detected a defective pulse oximeter sensor. At 356, the system determines if there is a defective pulse oximeter probe or if the probe is incompatible. At 360, the system determines if an error condition or defective operation alarm has been discovered by the blender system 34 and the blender system has reported that error via 36. Other integrity checks as depicted by 364 can also be carried out. In any of the above cases, an alarm is generated in accord with the type and severity of the error condition at 368.

Figure 7:
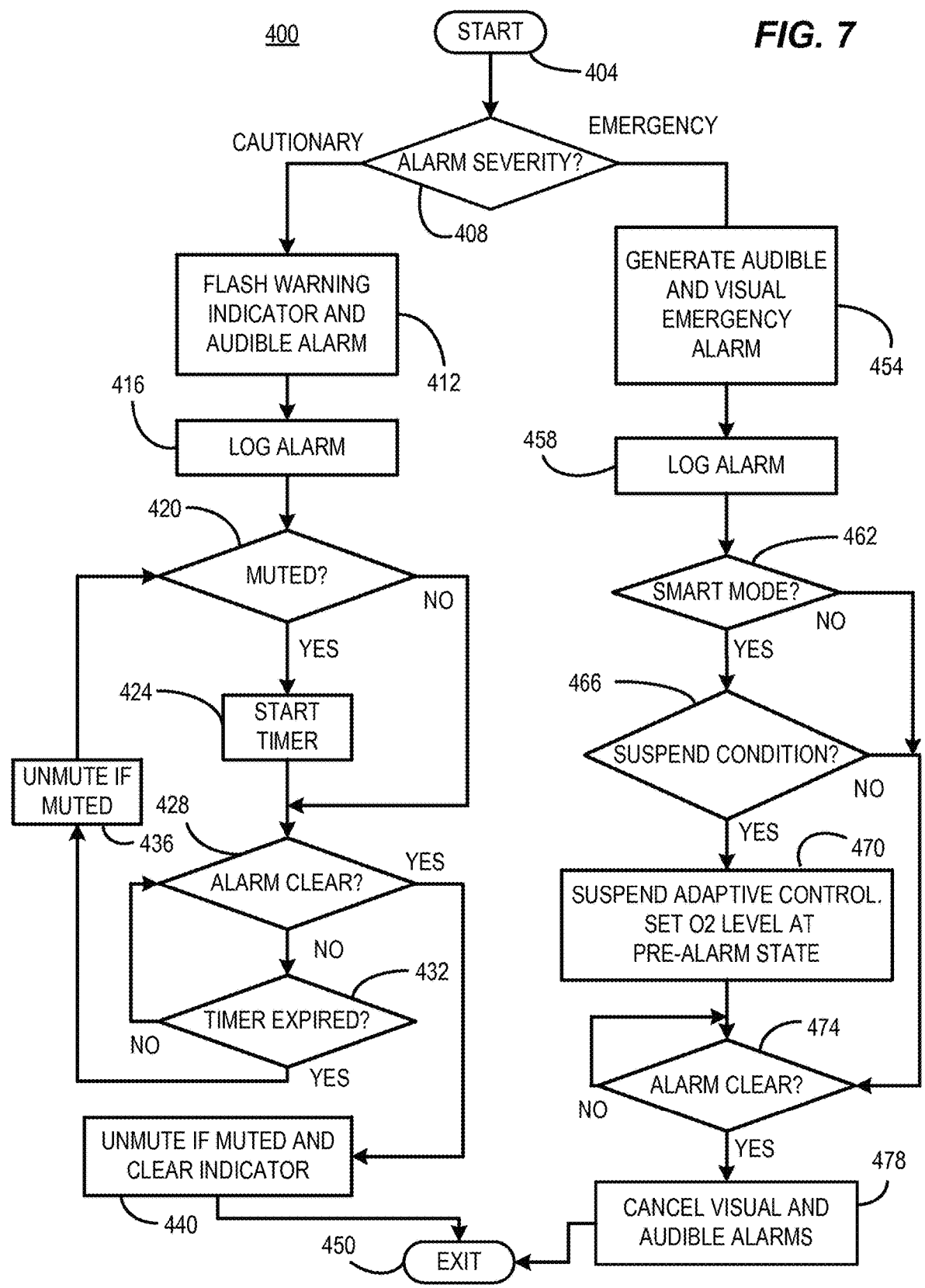
FIG. 7 is a flow chart of an example set of alarm operations consistent with certain example embodiments of the present invention.

Referring to FIG. 7, an example method 400 for processing alarms is depicted starting at 404. In this example implementation, two types of alarms are provided for so that the alarms are classified as either "cautionary" or "emergency". Those skilled in the art will appreciate upon consideration of the present teachings that other types of alarms and alarm processes can be devised upon consideration of the present teachings.

At 408 a determination is made as to the severity of the alarm. In most instances this may be as simple as an association between type of alarm and a designated severity. If the alarm is considered "cautionary", in this example a warning indicator is flashed at 412 and an audible alarm is generated. The alarm condition, time, etc. is logged to non-volatile storage at 416. In the cautionary alarm mode according to the present illustrative embodiment, the operator can manually mute the audible alarm. The muting, in this embodiment may only be temporary until the alarm is cleared. Once the alarm is sounding and displaying a flashing cautionary alarm indicator, the operator can mute the alarm by operation carried out at the user interface 30 and this condition is detected at 420. Once muted, a timer is started at 424 for a specified period of time (e.g., two minutes). The alarm condition is monitored at 428 to determine if the alarm condition has been cleared by resolution of the condition causing the alarm. If not cleared, the state of the timer is checked at 432. Once the timer expires, if the alarm condition has not been cleared at 428 the audible alarm is unmuted at 436 and control returns to 420.

Once the alarm condition has been cleared, as detected at 428, the audible alarm is unmuted and the visual indicator (flashing warning indicator) is cleared at 440 and the alarm process exits at 450. When, at 420, the alarm has not been muted, the timer operation is bypassed so that control passes from 420 to 428 and the process loops as shown until either the alarm is muted, or the alarm is cleared. Many variations are possible upon considering the present teachings.

If the type of alarm is of higher severity, the present example utilizes an "emergency" alarm as detected at 408. When an emergency alarm is detected at 408, an audible alarm which is distinctive from the cautionary alarm and a visual indication of an emergency alarm is generated at 454. In the present example, the alarm cannot be cleared manually, per se, except for example by reverting the adaptive controller system to standby or manual control or turning off the adaptive controller system.

The alarm is logged to non-volatile storage at 458 and the process determines if the system is operating in the smart mode (adaptive control of the blender system) at 462. If so, and the alarm is of a type that is configured to suspend the adaptive control of delivery of the blend of gasses to the patient at 466, then adaptive control is suspended at 470 and the gas mixture from the blender is set to the most recently set blend of gasses and control passes to 474. At this point, the blender system can be operated manually to adjust the blend of gasses based on the judgment of medical personnel. If, at 462, the system is not operating in smart mode, or if at 466, the alarm of a type that is configured to suspend operation of the smart mode, the process also proceeds to 474 where the system determines if the alarm condition has been cleared. The alarm condition remains as described until the alarm is determined to be cleared at 474, at which point, the visual and audible alarms are cleared at 478 and the process exits at 450.

Again many variations are possible in the emergency alarm condition including permitting the temporary muting of an audible alarm and clearing the alarm upon entering a manual control of the blender system. Other variations will occur to those skilled in the art upon consideration of the present teachings.

In accord with an example embodiment, detection of low perfusion results transition to the emergency alarm state. This is a condition in which the pulse oximeter data indicates data is not reliable for use by the processor 26. Similarly, if the pulse oximeter detects that the sensor is off the patient or not attached, processor 26 initiates an emergency alarm since pulse oximeter data is not reliable.

In the condition in which upper or lower $SpO_2$ alarm limits are exceeded, or the pulse rate upper and lower alarm limits are exceeded, the processor generates a cautionary alarm.

In certain embodiments, the system enters the standby state if the blender system tells the adaptive control system that an operator has made a manual adjustment to the blender system. In the event of a pressure loss is detected by the blender system of any or all gasses, an emergency alarm is initiated by the processor 26. A cautionary alarm is generated if the system detects that the battery's energy level does not exceed capability to maintain the adaptive controller 18 in operational mode for more than a designated amount of time, for example more than 5 minutes, AC power support. Similarly, a cautionary alarm is generated if the AC power disconnect is disconnected.

The type of alarm condition (cautionary or emergency) can be determined by the nature of the alarm that is detected. In cautionary alarms, according to an example implementation, a yellow warning indicator is illuminated and flashed.

The alarms may be logged to non-volatile memory information including, but not limited to a code corresponding to the alarm condition that was detected and a time representing the number of seconds since the last power on.

In emergency alarms, according to the present example, the alarm mode can be determined by the alarm detection function that caused the alarm to be invoked. Emergency alarms may be generated, for example, when the $SpO_2$ level crosses the upper or lower alarm limit. Similarly, an emergency alarm may be initiated upon detection that the pulse rate crosses the upper or lower pulse rate alarm limit, or when low perfusion is detected, or when the sensor is detected to be off the patient or disconnected; or when low pressure of any or all gasses is detected. Additionally, an emergency alarm may be generated if the system detects a communication failure between the adaptive controller system 18 and the blender system 34.

Many variations will occur to those skilled in the art upon consideration of the present teachings.

Thus, an adaptive controller system for control of a gas mixture for delivery to a patient via a separate external gas blender system has a pulse oximeter interface configured to receive data from a pulse oximeter. A gas blender interface is configured to send and receive data to and from the separate externally connected gas blender system. One or more processors are coupled to the pulse oximeter interface and the gas blender interface, the one or more processors being programmed to: receive pulse oximeter data via the pulse oximeter interface including $SpO_2$ level signals and alarm condition signals; output data to the gas blender interface to effect adaptive feedback control of the gas mixture based upon the $SpO_2$ level signals from the pulse oximeter interface; receive data via the gas blender interface including a signal indicating that the gas mixture delivered by the gas blender system has been manually changed; and upon receipt of the signal via the gas blender interface indicating that the gas mixture delivered by the gas blender system has been manually changed, enter a manual override mode and halt sending adaptive feedback control signals to the gas blender interface.

In certain implementations, the gas blender interface receives signals from a blender controller residing within the separate external gas blender system. In certain implementations, the adaptive feedback control is implemented using a proportional integral differential (PID) controller. In certain implementations, a lookup table relating $SpO_2$ levels to $PaO_2$ levels is provided and stored in adaptive controller storage, where in being programmed to effect adaptive feedback control, the one or more processors are configured to convert the $SpO_2$ level received via the pulse oximeter interface to a $PaO_2$ level for calculation of an appropriate gas mixture, and to calculate values of $PaO_2$ that are not present on the lookup table using interpolation.

In certain implementations, the one or more processors are further programmed to enter one of at least first and second alarm states upon detection of an alarm condition; where the first alarm state is associated with non-emergency alarm conditions and the second alarm state is associated with of emergency alarm conditions. In certain of the alarm conditions that result in the second alarm state, operation of the adaptive controller is halted and a manual override condition is initiated with the gas mixture initially set at a most recent gas mixture prior to entry into the second alarm state.

In certain implementations, a power source including a battery backup powers the adaptive controller system separately from the blender system. In certain implementations, the one or more programmed processors are programmed to receive a signal from the pulse oximeter interface that indicates that the pulse oximeter is not providing a reliable output and responsive thereto the one or more programmed processors are programmed to initiate an alarm condition. In certain implementations, the one or more processors are programmed to compare measured $SpO_2$ data received via the pulse oximeter interface with upper and lower alarm limits, and to initiate an alarm condition if the $SpO_2$ data is outside the alarm limits. In certain implementations, the one or more processors are programmed to compare measured gas temperature data received via the blender interface with upper and lower alarm limits, and to initiate an alarm condition if the temperature data is outside the alarm limits. In certain implementations, the one or more processors are programmed to compare measured data that is associated with gas humidity received via the blender interface with upper and lower alarm limits, and to initiate an alarm condition if the measured data is outside the alarm limits. In certain implementations, the one or more processors are programmed to compare measured data with alarm limits and to initiate an alarm condition if the measured data is outside the alarm limits; and the alarm condition has one of an emergency alarm and a cautionary alarm, where in the emergency alarm condition adaptive control is terminated and the blender is reverted to manual control with an initial value of most recently established value of the blend set under adaptive control.

Another adaptive controller system for control of a gas mixture for delivery to a patient via a separate external gas blender system has a pulse oximeter interface configured to receive data from a pulse oximeter. A gas blender interface is configured to send and receive data to and from a blender controller residing in the separate externally connected gas blender system. A lookup table that relates $SpO_2$ levels to $PaO_2$ levels is provided. One or more processors are coupled to the pulse oximeter interface and the gas blender interface, with the one or more processors being programmed to: receive pulse oximeter data via the pulse oximeter interface including $SpO_2$ level signals and alarm condition signals; convert the $SpO_2$ level received via the pulse oximeter interface to a $PaO_2$ level for calculation of an appropriate gas mixture, and to calculate values of PaO2 that are not present on the lookup table using interpolation; output data to the gas blender interface to effect adaptive feedback control of the gas mixture based upon the $SpO_2$ level signals from the pulse oximeter interface, where the adaptive feedback control is provided by a proportional integral differential (PID) controller; receive data via the gas blender interface including a signal indicating that the gas mixture delivered by the gas blender system has been manually changed; and upon receipt of the signal via the gas blender interface indicating that the gas mixture delivered by the gas blender system has been manually changed, enter a manual override mode and halt sending adaptive feedback control signals to the gas blender interface.

In certain implementations, the proportional integral differential (PID) controller is implemented using one or more of the programmed processors. In certain implementations, the one or more processors are programmed to compare at least one of measured gas temperature data and gas humidity related data received via the blender interface with upper and lower alarm limits, and to initiate an alarm condition if the temperature data or humidity data are outside the alarm limits. In certain implementations, the one or more processors are further programmed to enter one of at least first and second alarm states upon detection of an alarm condition, where the first alarm state associated with non-emergency alarm conditions and where the second alarm state associated with of emergency alarm conditions. In certain of the alarm conditions that result in the second alarm state, operation of the adaptive controller is halted and a manual override condition is initiated with the gas mixture initially set at a most recent gas mixture prior to entry into the second alarm state. In certain implementations, a power source including a battery backup powers the adaptive controller system separately from the blender system.

In certain implementations, the one or more programmed processors are further programmed to: receive a signal from the pulse oximeter interface that indicates that the pulse oximeter is not providing a reliable output, and to initiate an alarm condition in response thereto; compare measured $SpO_2$ data received via the pulse oximeter interface with upper and lower alarm limits, and to initiate an alarm condition if the $SpO_2$ data is outside the alarm limits; compare measured gas temperature data received via the blender interface with upper and lower alarm limits, and to initiate an alarm condition if the temperature data is outside the alarm limits; compare measured data that is associated with gas humidity received via the blender interface with upper and lower alarm limits; and to initiate an alarm condition if the measured data is outside the alarm limits. In certain implementations, the one or more processors are programmed to compare the measured data with alarm limits and to initiate an alarm condition if the measured data is outside the alarm limits.

A method, carried out in an adaptive control system, of control of a gas mixture for delivery to a patient via a separate external gas blender system in a manner consistent with certain embodiments of the present teachings involves receiving data from a pulse oximeter via a pulse oximeter interface configured to receive data from a pulse oximeter; sending and receiving data to and from the separate externally connected gas blender system via a gas blender interface. At one or more processors coupled to the pulse oximeter interface and the gas blender interface: receiving pulse oximeter data via the pulse oximeter interface including $SpO_2$ level signals and alarm condition signals; outputting data to the gas blender interface to effect adaptive feedback control of the gas mixture based upon the $SpO_2$ level signals from the pulse oximeter interface; receiving data via the gas blender interface including a signal indicating that the gas mixture delivered by the gas blender system has been manually changed; and upon receipt of the signal via the gas blender interface indicating that the gas mixture delivered by the gas blender system has been manually changed, entering a manual override mode and halting sending adaptive feedback control signals to the gas blender interface.

In certain implementations, the one or more processors causing entry into one of at least first and second alarm states upon detection of an alarm condition, where the first alarm state associated with non-emergency alarm conditions, where the second alarm state associated with of emergency alarm conditions, and where in certain of the alarm conditions that result in the second alarm state, the one or more processors causing operation of the adaptive controller to halt, and initiating a manual override state with the gas mixture initially set at a most recent gas mixture prior to entry into the second alarm state.

Those skilled in the art will recognize, upon consideration of the above teachings, that certain of the above exemplary embodiments are based upon use of a programmed processor. However, the invention is not limited to such exemplary embodiments, since other embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

An example embodiment of an adaptive gas mixture controller system as taught herein has a pulse oximeter interface receives pulse oximeter data. A gas blender interface communicates with a separate externally connected gas blender. A processor receives pulse oximeter data via the pulse oximeter interface and outputs data to the gas blender interface for adaptive feedback control of the gas mixture based upon the $SpO_2$ level signals from the pulse oximeter interface. When the processor receives data from the gas blender indicating that the gas mixture has been manually changed, enters a manual override mode and halts sending adaptive feedback control signals to the gas blender.

Certain example embodiments described herein, are or may be implemented using a programmed processor executing programming instructions that are broadly described above in flow chart form that can be stored on any suitable electronic or computer readable non-transitory storage medium (such as, for example, disc storage, Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies), where the term "non-transitory" is intended to exclude propagating signals but not memory that can be rewritten or which loses its data when powered down. However, those skilled in the art will appreciate, upon consideration of the present teaching, that the processes described above can be implemented in any number of variations and in many suitable programming languages without departing from embodiments of the present invention. For example, the order of certain operations carried out can often be varied, additional operations can be added or operations can be deleted without departing from certain example embodiments of the invention. Error trapping can be added and/or enhanced and variations can be made in user interface and information presentation without departing from certain example embodiments of the present invention. Such variations are contemplated and considered equivalent.

While certain illustrative embodiments have been described, it is evident that many alternatives, modifications, permutations and variations will become apparent to those skilled in the art in light of the foregoing description.

What is claimed is:

1. A system for adaptive control of delivery of a breathing gas mixture to a patient, the system comprising:
    a gas blender including a first input for connection with an oxygen source and a second input for connection with a compressed air source;
    a pulse oximeter interface configured to receive signals from a pulse oximeter indicative of a current blood oxygen level of the patient;
    a controller coupled to the gas blender and the pulse oximeter interface;
    wherein the controller is configured to:
        receive, from the gas blender, data indicative of a current mixture of gases provided to the patient;
        receive, from the pulse oximeter interface, the signals from the pulse oximeter indicative of a current blood oxygen level of the patient;
        compare the signals indicative of the current blood oxygen level of the patient to a target blood oxygen level;
        determine an appropriate change to the current mixture of gases provided to the patient to achieve a change in a percentage of oxygen in the breathing gas mixture;
        alter the percentage of oxygen in the breathing gas mixture by adjusting input of one or both of oxygen or compressed air to the gas blender; and
        receive new signals from the pulse oximeter interface indicative of a current blood oxygen level of the patient.

2. The system of claim 1, further comprising a heater for heating the breathing gas mixture coupled to the gas blender, and a humidifier for humidifying the breathing gas mixture coupled to the gas blender.

3. The system of claim 1, wherein the gas blender further comprises a first valve controlling the first input and a second valve controlling the second input to the gas blender.

4. The system of claim 3, wherein the controller is configured to perform an adjustment to one or more of the first valve and the second valve to achieve the change in the percentage of oxygen in the breathing gas mixture.

5. The system of claim 1, wherein the signals received at the pulse oximeter interface from the pulse oximeter include an $SpO_2$ level of the patient.

6. The system of claim 5, wherein the signals received at the pulse oximeter interface from the pulse oximeter include a pulse rate of the patient.

7. The system of claim 5, wherein the controller further comprises a memory, the memory storing a lookup table relating $SpO_2$ levels to $PaO_2$ levels, wherein the lookup table is derived from a sigmoid shaped oxyhemoglobin dissociation curve.

8. The system of claim 7, wherein the controller comprises a proportional integral derivative (PID) controller configured to track the sigmoid shaped oxyhemoglobin dissociation curve.

9. The system of claim 8, wherein the controller is further configured to determine a $PaO_2$ level from the $SpO_2$ level of the patient for calculation of an appropriate gas mixture.

10. The system of claim 9, wherein the controller is further configured to determine the change in the percentage of oxygen in the breathing gas mixture based on the calculation of the appropriate gas mixture.

11. The system of claim 10, further comprising one or more sensors for measuring one or more characteristics of the breathing gas mixture and configured to provide the one or more measured characteristics to the controller, wherein the one or more characteristics of the breathing gas mixture include a temperature of the breathing gas mixture, a humidity of the breathing gas mixture, and a flow rate of the breathing gas mixture.

12. The system of claim 11, the controller further configured to:
    receive, from the gas blender, signals indicative of a current humidification level of the breathing gas mixture;
    compare the current humidification level of the breathing gas mixture to a target humidification level; and alter the current humidification level of the breathing gas mixture in the gas blender.

13. The system of claim 1, further comprising a patient interface coupled to an outlet of the gas blender, the patient interface comprising a nasal cannula.

14. An adaptive control system for control of a gas mixture for delivery to a patient via a gas blender system, the system comprising:
   a pulse oximeter interface configured to receive $SpO_2$ signals from a pulse oximeter indicative of a current blood oxygen level of the patient;
   a gas blender including a first input for connection with an oxygen source and a second input for connection with a compressed air source, the gas blender configured to produce a gas mixture; and
   a controller coupled to the pulse oximeter interface and the gas blender, the controller configured to:
      receive first $SpO_2$ signals from the pulse oximeter indicative of a current blood oxygen level of the patient at a first time;
      determine, from the first $SpO_2$ signals, a first $PaO_2$ level at the first time using a lookup table, wherein the lookup table is derived from a sigmoid shaped oxyhemoglobin dissociation curve;
      receive, from the gas blender, a signal indicative of a current gas mixture;
      determine an appropriate change to the current gas mixture based on the first $PaO_2$ level;
      adjust at least one of the first input and the second input of the gas blender to produce the appropriate change to the gas mixture by altering the input of one or both of oxygen or compressed air to the gas blender; and
      receive second $SpO_2$ signals from the pulse oximeter indicative of a current blood oxygen level of the patient at a second time.

15. The system of claim 14, wherein the controller is further configured to:
   determine, from the second $SpO_2$ signals, a second $PaO_2$ level at the second time using the lookup table.

16. The system of claim 15, wherein the controller is further configured to:
   compare the second $PaO_2$ level to the first $PaO_2$ level; and
   generate an indication of the comparison for display.

17. The system of claim 15, wherein the controller is further configured to:
   compare an $SpO_2$ level from the second $SpO_2$ signals to a predetermined upper and lower limits; and
   initiate an alarm condition if the $SpO_2$ level is outside the predetermined upper and lower limits.

18. The system of claim 15, wherein the controller is further configured to:
   determine an appropriate second change to the current gas mixture based on the second $PaO_2$ level; and
   adjust at least one of the first input and the second input of the gas blender to produce the appropriate second change to the gas mixture by altering the input of one or both of oxygen or compressed air to the gas blender.

19. The system of claim 14, wherein the controller comprises a proportional integral derivative (PID) controller configured to track the sigmoid shaped oxyhemoglobin dissociation curve.

20. The system of claim 14, the controller further configured to:
   upon receiving a signal from the gas blender that the gas mixture delivered by the gas blender system has been manually changed, entering a manual override mode halting adaptive feedback control signals to the gas blender.

21. A system for delivery of a breathing gas mixture to a patient, the system comprising:
   a first input for connection with an oxygen source, wherein the first input provides a flow of oxygen;
   a second input for connection with a compressed air source, wherein the second input provides a flow of air, wherein the flow of oxygen is mixed with the flow of air to form a breathing gas mixture;
   a humidifier comprising a water reservoir and a vaporization mechanism for humidifying the breathing gas mixture to output a humidified breathing gas mixture;
   a patient interface in fluid communication with the humidifier and configured to deliver the humidified breathing gas mixture to the patient;
   a pulse oximeter interface configured to receive signals from a pulse oximeter indicative of a current blood oxygen level of the patient;
   a controller coupled to the pulse oximeter interface and having a memory, wherein the controller is configured to:
      receive signals relating to a current proportion of air and oxygen in the breathing gas mixture;
      receive, from the pulse oximeter interface, the signals from the pulse oximeter indicative of a current blood oxygen level of the patient;
      compare the signals indicative of the current blood oxygen level of the patient to a target blood oxygen level;
      based on the current proportion of air and oxygen in the breathing gas mixture and the comparison of current blood oxygen level to the target blood oxygen level, determine an appropriate change to the breathing gas mixture to achieve an adjustment in a percentage of oxygen in the breathing gas mixture;
      based on the determined appropriate change, alter the percentage of oxygen in the breathing gas mixture by adjusting input of one or both of oxygen or compressed air; and
      receive new signals from the pulse oximeter interface indicative of a new current blood oxygen level of the patient.

22. The system of claim 21, further comprising a heating device for heating the humidified breathing gas mixture.

23. The system of claim 22, further comprising a delivery tube configured to convey the heated and humidified breathing gas mixture to the patient interface configured for delivery of the heated and humidified breathing gas mixture to the patient.

24. The system of claim 23, wherein the patient interface is a nasal cannula.

25. The system of claim 24, wherein the heating device is a heated wire.

26. The system of claim 25, wherein the heated wire is disposed upstream of the nasal cannula.

27. The system of claim 26, wherein the heated wire is disposed upstream of the humidifier.

28. The system of claim 21, wherein the vaporization mechanism comprises a heater for heating water in the water reservoir to steam.

29. The system of claim 28, wherein the controller is coupled to the humidifier and configured to adjust a humidification level of the humidifier.

30. The system of claim 21, wherein the signals received at the pulse oximeter interface from the pulse oximeter include an SpO2 level of the patient.

31. The system of claim 30, wherein the signals received at the pulse oximeter interface from the pulse oximeter include a pulse rate of the patient.

32. The system of claim 30, wherein the memory stores a lookup table relating SpO2 levels to PaO2 levels, and the lookup table is derived from a sigmoid shaped oxyhemoglobin dissociation curve.

33. The system of claim 32, wherein the controller comprises a proportional integral derivative (PID) controller configured to track the sigmoid shaped oxyhemoglobin dissociation curve.

34. The system of claim 33, wherein the controller is further configured to:
convert the SpO2 level of the patient to a Pa)2 level for calculation of an appropriate gas mixture.

35. The system of claim 21, wherein the first input comprises a valve operatively coupled to the controller.

36. The system of claim 21, wherein the compressed air source is external to the system.

37. The system of claim 21, wherein the controller is configured to:
adjust the first input by actuating a valve, based on the calculated appropriate change, to achieve the adjustment in oxygen percentage of the breathing gas mixture.

38. A method for preparing a breathing gas mixture using a gas blending system, comprising:
mixing an air flow at a first flow rate with an oxygen flow at a second flow rate to form a breathing gas mixture at a third flow rate;
receiving, at a controller, first signals relating to a current proportion of air and oxygen in the breathing gas mixture;
receiving, at the controller, from a pulse oximeter interface, second signals from a pulse oximeter indicative of a first blood oxygen level of a patient;
comparing the second signals indicative of the first blood oxygen level to a target blood oxygen level;
based on the current proportion of air and oxygen in the breathing gas mixture and the comparison of the second signals indicative of the first blood oxygen level to the target blood oxygen level, determining an appropriate change to the breathing gas mixture to achieve an adjustment in a percentage of oxygen in the breathing gas mixture;
altering the percentage of oxygen in the breathing gas mixture by adjusting one or both of the first flow rate and the second flow rate, based on the calculated appropriate adjustment; and
receiving third signals from the pulse oximeter interface indicative of a second blood oxygen level of the patient.

39. The method of claim 38, further comprising:
humidifying the breathing gas mixture at a level of humidification by vaporizing water in a humidifier.

40. The method of claim 39, further comprising:
measuring a water consumption rate of the humidifier; and
determining a current humidification level based on the third flow rate and the water consumption rate.

41. The method of claim 40, further comprising:
adjusting the level of humidification of the breathing gas mixture in the humidifier from the current humidification level to a target humidification level.

42. The method of claim 39, further comprising:
heating the breathing gas mixture with a heating device.

43. The method of claim 38, further comprising:
conveying the breathing gas mixture to a patient via at least one of a delivery tube and a nasal cannula.

44. The method of claim 38, wherein altering the percentage of oxygen in the breathing gas mixture comprises adjusting the second flow rate by actuating a valve, based on the calculated appropriate adjustment, to achieve the adjusment oxygen percentage of the breathing gas mixture.

* * * * *